United States Patent
Casey et al.

(10) Patent No.: US 12,127,769 B2
(45) Date of Patent: Oct. 29, 2024

(54) PATIENT-SPECIFIC JIG FOR PERSONALIZED SURGERY

(71) Applicant: Carlsmed, Inc., Carlsbad, CA (US)

(72) Inventors: Niall Patrick Casey, Carlsbad, CA (US); Michael J. Cordonnier, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 215 days.

(21) Appl. No.: 17/531,417

(22) Filed: Nov. 19, 2021

(65) Prior Publication Data
US 2022/0160405 A1    May 26, 2022

Related U.S. Application Data

(60) Provisional application No. 63/116,436, filed on Nov. 20, 2020.

(51) Int. Cl.
*A61B 17/70*  (2006.01)
*A61B 17/00*  (2006.01)

(52) U.S. Cl.
CPC .... *A61B 17/7074* (2013.01); *A61B 2017/00526* (2013.01); *A61B 2017/00955* (2013.01); *A61B 2017/00982* (2013.01)

(58) Field of Classification Search
CPC ...... A61B 2017/00955; A61B 17/7074; A61B 2017/00526; A61B 2017/00982; A61B 17/7011; A61B 2017/568; A61B 2034/108; A61B 2034/104
USPC ................................................. 606/250–279
See application file for complete search history.

(56) References Cited

U.S. PATENT DOCUMENTS

| | | | |
|---|---|---|---|
| 4,704,686 A | 11/1987 | Aldinger | |
| 4,936,862 A | 6/1990 | Walker et al. | |
| 5,431,562 A | 7/1995 | Andreiko et al. | |
| D420,995 S | 2/2000 | Imamura | |
| D436,580 S | 1/2001 | Navano | |
| 6,315,553 B1 | 11/2001 | Sachdeva | |

(Continued)

FOREIGN PATENT DOCUMENTS

| | | |
|---|---|---|
| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Eduardo C Robert
*Assistant Examiner* — Tara Rose E Carter
(74) *Attorney, Agent, or Firm* — Perkins Coie LLP

(57) ABSTRACT

A patient-specific jig for confirming a correct contour of a fixation element in an operative setting, the patient-specific jig including a jig body having a top end and a bottom end provided at opposite ends of a longitudinal axis of the jig body, and an inner contour guide disposed in a front surface of the jig body, the inner contour guide having a shaped cross-section and being shaped in a contoured curve along the longitudinal axis of the jig body, wherein the contoured curve conforms to a set of patient-specific geometric parameters.

59 Claims, 15 Drawing Sheets

(56) References Cited

U.S. PATENT DOCUMENTS

| | | |
|---|---|---|
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| D958,151 S | 7/2022 | Casey et al. |
| 11,376,054 B2 * | 7/2022 | Kemper ............... A61B 17/80 |
| 11,806,241 B1 | 11/2023 | Hussain et al. |
| 2002/0007294 A1 | 1/2002 | Bradbury et al. |
| 2004/0104512 A1 | 6/2004 | Eidenschink |
| 2004/0171924 A1 | 9/2004 | Mire et al. |
| 2005/0049590 A1 | 3/2005 | Alleyne et al. |
| 2005/0271996 A1 | 12/2005 | Sporbert et al. |
| 2006/0009780 A1 | 1/2006 | Foley |
| 2007/0118243 A1 | 5/2007 | Schroeder |
| 2007/0276501 A1 | 11/2007 | Betz |
| 2008/0161680 A1 | 7/2008 | von Jako |
| 2008/0195240 A1 | 8/2008 | Martin |
| 2008/0227047 A1 | 9/2008 | Lowe |
| 2009/0062739 A1 | 3/2009 | Anderson |
| 2010/0191088 A1 | 7/2010 | Anderson |
| 2010/0292963 A1 | 11/2010 | Schroeder |
| 2010/0324692 A1 | 12/2010 | Uthgenannt |
| 2011/0218545 A1 | 9/2011 | Catanzarite et al. |
| 2011/0301710 A1 | 12/2011 | Mather et al. |
| 2012/0010710 A1 | 1/2012 | Frigg |
| 2012/0084064 A1 | 4/2012 | Dzenis et al. |
| 2012/0116203 A1 | 5/2012 | Vancraen |

(56) References Cited

U.S. PATENT DOCUMENTS

| | | | |
|---|---|---|---|
| 2012/0150243 | A9 | 6/2012 | Crawford |
| 2012/0191192 | A1 | 7/2012 | Park |
| 2012/0287238 | A1 | 11/2012 | Onishi |
| 2012/0296433 | A1 | 11/2012 | Farin |
| 2012/0322018 | A1 | 12/2012 | Lowe |
| 2013/0211531 | A1 | 8/2013 | Steines et al. |
| 2013/0323669 | A1 | 12/2013 | Lowe |
| 2014/0072608 | A1 | 3/2014 | Karagkiozaki |
| 2014/0074438 | A1 | 3/2014 | Furrer |
| 2014/0081659 | A1 | 3/2014 | Nawana et al. |
| 2014/0086780 | A1 | 3/2014 | Miller |
| 2014/0100886 | A1 | 4/2014 | Woods |
| 2014/0164022 | A1 | 6/2014 | Reed |
| 2014/0263674 | A1 | 9/2014 | Cerveny |
| 2014/0350614 | A1 | 11/2014 | Frey |
| 2015/0079533 | A1 | 3/2015 | Lowe |
| 2015/0105891 | A1 | 4/2015 | Golway et al. |
| 2015/0199488 | A1 | 7/2015 | Falchuk |
| 2015/0213225 | A1 | 7/2015 | Amarasingham |
| 2015/0324490 | A1 | 11/2015 | Page |
| 2015/0328004 | A1 | 11/2015 | Mafhouz |
| 2015/0332018 | A1 | 11/2015 | Rosen |
| 2016/0001039 | A1 | 1/2016 | Armour et al. |
| 2016/0015465 | A1 | 1/2016 | Steines et al. |
| 2016/0030067 | A1 | 2/2016 | Frey et al. |
| 2016/0074048 | A1 | 3/2016 | Pavlovskaia |
| 2016/0117817 | A1 | 4/2016 | Seel |
| 2016/0143744 | A1 | 5/2016 | Bojarski et al. |
| 2016/0184054 | A1 | 6/2016 | Lowe |
| 2016/0210374 | A1 | 7/2016 | Mosnier et al. |
| 2016/0217268 | A1 | 7/2016 | Otto |
| 2016/0242857 | A1 | 8/2016 | Scholl |
| 2016/0300026 | A1 | 10/2016 | Bogoni et al. |
| 2016/0354039 | A1 | 12/2016 | Soto et al. |
| 2016/0378919 | A1 | 12/2016 | McNutt et al. |
| 2017/0000566 | A1 | 1/2017 | Gordon |
| 2017/0014169 | A1 | 1/2017 | Dean |
| 2017/0020679 | A1 | 1/2017 | Maclennan |
| 2017/0035514 | A1 | 2/2017 | Fox et al. |
| 2017/0061375 | A1 | 3/2017 | Laster |
| 2017/0068792 | A1 | 3/2017 | Reiner |
| 2017/0135706 | A1 | 5/2017 | Frey et al. |
| 2017/0143494 | A1 | 5/2017 | Mahfouz |
| 2017/0143831 | A1 | 5/2017 | Varanasi et al. |
| 2017/0216047 | A1 | 8/2017 | Hawkes et al. |
| 2017/0220740 | A1 | 8/2017 | D'Urso |
| 2017/0252107 | A1 | 9/2017 | Turner et al. |
| 2017/0262595 | A1 | 9/2017 | Vorhis |
| 2017/0340447 | A1 | 11/2017 | Mahfouz |
| 2017/0354510 | A1 | 12/2017 | O'Neil et al. |
| 2017/0367645 | A1 | 12/2017 | Klinder |
| 2018/0008349 | A1 | 1/2018 | Gillman |
| 2018/0113992 | A1 | 4/2018 | Eltorai et al. |
| 2018/0116727 | A1 | 5/2018 | Caldwell et al. |
| 2018/0168499 | A1 | 6/2018 | Bergold |
| 2018/0168731 | A1 | 6/2018 | Reid |
| 2018/0185075 | A1 | 7/2018 | She |
| 2018/0233222 | A1 | 8/2018 | Daley |
| 2018/0233225 | A1 | 8/2018 | Experton |
| 2018/0250075 | A1 | 9/2018 | Cho |
| 2018/0303552 | A1 | 10/2018 | Ryan |
| 2018/0303616 | A1* | 10/2018 | Bhattacharyya ....... B33Y 50/02 |
| 2018/0308569 | A1 | 10/2018 | Luellen |
| 2018/0338841 | A1 | 11/2018 | Miller et al. |
| 2019/0065685 | A1 | 2/2019 | Pickover |
| 2019/0201106 | A1 | 7/2019 | Siemionow |
| 2019/0262084 | A1 | 8/2019 | Roh et al. |
| 2019/0266597 | A1 | 8/2019 | Mohtar |
| 2019/0282367 | A1 | 9/2019 | Casey et al. |
| 2019/0321193 | A1* | 10/2019 | Casey ................ A61B 17/7058 |
| 2019/0328929 | A1 | 10/2019 | Kugler et al. |
| 2019/0333622 | A1 | 10/2019 | Levin |
| 2019/0354693 | A1 | 11/2019 | Yoon |
| 2019/0380792 | A1 | 12/2019 | Poltaretskyi et al. |
| 2020/0021570 | A1 | 1/2020 | Lin |
| 2020/0078180 | A1 | 3/2020 | Casey et al. |
| 2020/0085509 | A1 | 3/2020 | Roh et al. |
| 2020/0170802 | A1 | 6/2020 | Casey et al. |
| 2020/0261156 | A1 | 8/2020 | Schmidt |
| 2020/0289288 | A1 | 9/2020 | Müller et al. |
| 2020/0315708 | A1 | 10/2020 | Mosnier et al. |
| 2021/0059822 | A1 | 3/2021 | Casey et al. |
| 2021/0064605 | A1 | 3/2021 | Balint |
| 2021/0145519 | A1 | 5/2021 | Mosnier et al. |
| 2021/0210189 | A1 | 7/2021 | Casey et al. |
| 2021/0287770 | A1 | 9/2021 | Anderson |
| 2021/0382457 | A1 | 12/2021 | Roh et al. |
| 2022/0000556 | A1 | 1/2022 | Casey et al. |
| 2022/0000625 | A1 | 1/2022 | Cordonnier |
| 2022/0006642 | A1 | 1/2022 | Maj et al. |
| 2022/0039965 | A1 | 2/2022 | Casey et al. |
| 2022/0047402 | A1 | 2/2022 | Casey et al. |
| 2022/0110686 | A1 | 4/2022 | Roh et al. |
| 2022/0160518 | A1 | 5/2022 | Casey et al. |
| 2022/0211507 | A1 | 7/2022 | Simoes et al. |

FOREIGN PATENT DOCUMENTS

| | | | |
|---|---|---|---|
| CN | 204468348 U | 7/2015 | |
| CN | 105796214 A | 7/2016 | |
| CN | 106202861 | 12/2016 | |
| CN | 107220933 | 9/2017 | |
| CN | 108670506 A | 10/2018 | |
| CN | 110575289 A | 12/2019 | |
| CN | 111281613 A | 6/2020 | |
| CN | 112155792 A | 1/2021 | |
| CN | 113643790 | 11/2021 | |
| EP | 3120796 A1 | 1/2017 | |
| WO | 9507509 | 3/1995 | |
| WO | 2004110309 A2 | 12/2004 | |
| WO | 2010151564 A1 | 12/2010 | |
| WO | 2012154534 | 11/2012 | |
| WO | 2014180972 A2 | 11/2014 | |
| WO | 2016172694 A1 | 10/2016 | |
| WO | WO-2018203100 A1 * | 11/2018 | ......... A61B 17/7002 |
| WO | 2019112917 A1 | 6/2019 | |
| WO | 2019148154 A1 | 8/2019 | |
| WO | 2022045956 | 3/2022 | |

OTHER PUBLICATIONS

Extended European Search Report for European Application No. 18885367.5, mailed Aug. 16, 2021, 8 pages.

International Search Report and Written Opinion for International Application No. PCT/US19/50885, mailed Jan. 28, 2020, 21 pages.

International Search Report and Written Opinion for International Application No. PCT/US19/63855, mailed Feb. 14, 2020, 15 pages.

International Search Report and Written Opinion for International Application No. PCT/US21/44878, mailed Nov. 16, 2021, 18 pages.

International Search Report and Written Opinion for International Application No. PCT/US21/45503, mailed Jan. 11, 2022, 19 pages.

International Search Report and Written Opinion for International Patent Application No. PCT/US2018/063530, mailed Feb. 12, 2019, 16 pages.

International Search Report and Written Opinion for International Patent Application No. PCT/US21/12065, mailed Apr. 29, 2021, 19 pages.

International Search Report and Written Opinion for International Patent Application No. PCT/US21/59837, mailed Feb. 7, 2022, 19 pages.

Majdouline et al., "Preoperative assessment and evaluation of instrumentation strategies for the treatment of adolescent idiopathic scoliosis: computer simulation and optimization." Scoliosis 7, 21 (2012), pp. 1-8.

Materialise Mimics, "Efficiently turn scans into accurate virtual 3D models," Retrieved on Nov. 1, 2019 at www. materialize.com/en/medical/software/mimics, 1 page.

Pimenta, Dr. Luiz, "Current Surgical Strategies to Restore Proper Sagittal Alignment," Journal of Spine 2015, vol. 4, Issue 4, 2 pages.

U.S. Appl. No. 15/958,409 for Ryan, filed Apr. 21, 2017.

(56) References Cited

OTHER PUBLICATIONS

Eshkalak, S.K. et al., "The role of three-dimensional printing in healthcare and medicine." Materials and Design 194, Jul. 10, 20202, 15 pages.
Extended European Search Report for European Application No. 19859930.0, mailed Jun. 22, 2022, 7 pages.
International Search Report and Written Opinion for International Patent Application No. PCT/US21/60074, mailed Mar. 17, 2022, 21 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
ISA: United States Patent and Trademark Office, International Search Report and Written Opinion for International Patent Application No. PCT/US23/33404, mailed Nov. 1, 2023, 11 pages.

* cited by examiner

PATIENT-SPECIFIC JIG FOR PERSONALIZED SURGERY

CROSS-REFERENCE TO RELATED APPLICATION

This application claims priority to and the benefit of U.S. Patent Application No. 63/116,436, filed Nov. 20, 2021, which is incorporated by reference in its entirety.

FIELD OF THE INVENTION

The invention described herein relates to a jig or template that can be used during surgery to confirm that a bent and contoured longitudinal fixation element, such as a fixation rod, conforms to predetermined parameters of a patient-specific pre-operative plan.

BACKGROUND

Orthopedic implants are used to correct a variety of different maladies. Orthopedic surgery utilizing orthopedic implants may include one of several specialties, including: hand surgery, shoulder and elbow surgery, total joint reconstruction (arthroplasty), skull reconstruction, maxillofacial reconstruction, pediatric orthopedics, foot and ankle surgery, spine surgery, musculoskeletal oncology, surgical sports medicine, and orthopedic trauma. Spine surgery may encompass one or more of the cervical, thoracic, lumbar spine, sacrum, pelvis, or ilium, and may treat a deformity or degeneration of the spine, or related back pain, leg pain, or other body pain. Irregular spinal curvature may include scoliosis, lordosis, or kyphosis (hyper- or hypo-). Irregular spinal displacement may include spondylolisthesis. Other spinal disorders include osteoarthritis, lumbar degenerative disc disease or cervical degenerative disc disease, lumbar spinal stenosis, or cervical spinal stenosis.

Spinal fusion surgery may be performed to set and hold purposeful changes imparted on the spine. Spinal surgeries typically include hardware or implants to help fix the relationship between anatomical structures such as vertebral bodies and nerves. In many instances, fixation devices or implants are affixed to bony anatomy to provide support during healing. These fixation implants are often made of polymers or metals (including titanium, titanium alloy, stainless steel, cobalt chrome, or other alloys), and can include types of bone anchors such as anchors, screws, nuts, bolts, and rivets for example, types of longitudinal fixation elements such as rods or other shaped longitudinal fixation elements, and also can include connectors, tethers, and other fasteners. Each implant may be designed to mate with the anatomy or other implants in order to provide a construct to allow relief of symptoms and encourage biologic healing. For example, bone anchors, such as pedicle screws, are typically connected by one or more longitudinal fixation elements, such as fixation rods, to provide stability and alignment during spinal fusion.

Spinal surgeons are often relied upon to treat patients with spinal deformities, such as scoliosis. These surgical treatments may require re-alignment of spinal anatomy and preservation of the re-alignment in order to relieve symptoms. Surgeons manipulate the spine using instruments and implants, such as intervertebral body fusion devices, that mate with bony anatomy. Adjustment of the instruments and implants connected to the bony anatomy can produce the desired alignment of the spinal anatomy. When the alignment of the spinal anatomy is achieved intra-operatively, the preservation of that alignment is required in order to provide post-operative relief of symptoms. Fixation implants can be used to provide a construct to maintain the correction achieved by the surgeon while post-operative bony fusion occurs.

Additionally, spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion). One goal of interbody fusion is to grow bone between vertebrae in order to seize (e.g., lock) the spatial relationships in a position that provides enough room for neural elements, including exiting nerve roots. An interbody implant (interbody device, intervertebral body fusion device, interbody implant, interbody cage, fusion cage, or spine cage) is a prosthesis that is used between vertebral bodies of the patient in spinal fusion procedures to maintain a desired relative position and alignment of the vertebrae and establish appropriate foraminal height and decompression of exiting nerves.

As mentioned above, fixation implants or devices, such as anchors, screws, nuts, bolts, rivets, rods, connectors, tethers, or other fasteners, are often affixed to the bony anatomy of the spine in an operative setting to maintain a desired relative position and alignment of the vertebrae and to provide support during healing. A longitudinal fixation element, such as a rod (or more than one rod), is typically used along with bone anchors, such as pedicle screws, as a fixation device in an operative setting to maintain the desired relative position and alignment of the vertebrae established by the surgeon. Each patient may have individual or unique anatomical geometry and disease characteristics but, unfortunately, most available fixation implants and devices, such as rods, have standard sizes and shapes.

In order to adjust a longitudinal fixation element, such as a rod, in an operative setting to accommodate the desired relative position and alignment of the treated segments of the spine, the surgeon typically uses one or more tools to manually bend and contour the rod. Typical tools for manually bending a rod in a surgical setting are French rod benders and in-situ benders. Manual bending of a rod in the operative setting can lead to inaccuracies in achieving the optimal spinal alignment due to limitations of the bending tool used and imprecise movements and manipulation of the tool by the surgeon. In addition, excessive manual bending of a rod can result in premature instrumentation failure of the rod because of inappropriate stress and/or fatigue of the rod material caused by the excessive bending or because of damage to the rod, such as notching.

As an alternative, a surgeon may determine an appropriate contour of a rod for a patient prior to the surgery and then have pre-contoured rods specifically made according to the appropriate contour for that patient and delivered to the operative setting for the patient's surgery. Such custom pre-contoured rods might be made by a custom medical device manufacturer or provider, or by a medical technician in a health care facility. The making of such custom pre-contoured rods, however, may be time-consuming and therefore require significant lead time on behalf of the surgeon and may also be cost prohibitive for many patient conditions and surgical situations.

SUMMARY OF THE INVENTION

In an aspect, a patient-specific jig is provided for confirming a correct contour of a fixation element in an operative setting, the patient-specific jig including a jig body having a top end and a bottom end provided at opposite ends of a longitudinal axis of the jig body, and an inner contour guide disposed in a front surface of the jig body, the inner contour guide having a shaped cross-section and being shaped in a contoured curve along the longitudinal axis of the jig body, wherein the contoured curve conforms to a set of patient-specific geometric parameters.

In another aspect, a patient-specific jig is provided for confirming a correct contour of a fixation element in an operative setting, the patient-specific jig including a contoured rigid member disposed along a longitudinal axis of the patient-specific jig, the contoured rigid member having a contoured curve that conforms to a set of patient-specific geometric parameters, and a plurality of jig segments connected to the contoured rigid member, each jig segment having an inner contour guide embedded in a front surface of the jig segment, the inner contour guide having a shaped cross-section.

A further aspect is directed to a method for manufacturing a patient-specific jig for use in confirming a correct contour of a fixation element in an operative setting, the method including the steps of accessing a data file containing patient-specific geometric parameters associated with a patient-specific pre-operative plan, converting the patient-specific geometric parameters into a machine data set for use by a three-dimensional production machine, and sending the machine data set to the three-dimensional production machine upon which the patient-specific jig is produced by the three-dimensional production machine in accordance with the machine data set.

In yet another aspect, a patient-specific jig is manufactured by a process of accessing a data file containing patient-specific geometric parameters associated with a patient-specific pre-operative plan, converting the patient-specific geometric parameters into a machine data set for use by a three-dimensional production machine, and sending the machine data set to the three-dimensional production machine upon which the patient-specific jig is produced by the three-dimensional production machine in accordance with the machine data set.

Another aspect is directed to a method for using a patient-specific jig to confirm a correct contour of a fixation element in an operative setting, the method including manually bending the fixation element using a tool during a patient operation in the operative setting, accessing the patient-specific jig in the operative setting, placing the fixation element against an inner contour guide of the patient-specific jig using proper orientation of the fixation element relative to the patient-specific jig, and confirming by visual and physical inspection whether the fixation element conforms to a contoured shape of the inner contour guide of the patient-specific jig.

In a further aspect, a method is provided for manufacturing a patient-specific jig by a medical device manufacturer, the method including accessing a data file containing patient-specific geometric parameters associated with a patient-specific pre-operative plan, converting the patient-specific geometric parameters into a machine data set for use by a three-dimensional production machine provided at a facility of the medical device manufacturer, sending the machine data set to the three-dimensional production machine, producing the patient-specific jig with the three-dimensional production machine in accordance with the machine data set, and sending the patient-specific jig from the medical device manufacturer to a medical care facility where an operative procedure is scheduled to be performed on a patient associated with the patient-specific pre-operative plan.

In another aspect, a method is provided for manufacturing a patient-specific jig at a medical care facility, the method including the steps of accessing, at the medical care facility, a data file containing patient-specific geometric parameters associated with a patient-specific pre-operative plan, converting the patient-specific geometric parameters into a machine data set for use by a three-dimensional production machine provided at the medical care facility, sending the machine data set to the three-dimensional production machine, and producing the patient-specific jig with the three-dimensional production machine in accordance with the machine data set.

In an aspect, a method is provided for manufacturing a patient-specific jig, the method including the steps of accessing a data file containing imaging data that represents bony anatomy associated with a patient, correcting anatomical relationships of the bony anatomy in a virtual space (e.g., a virtual model, a virtual simulation, an interactive representation of the patient's anatomy and/or anatomical relationships, etc.), modelling a path of a fixation element between a plurality of bony anatomical landmarks associated with the corrected anatomical relationships of the bony anatomy, and producing a patient-specific jig with a three-dimensional production machine, wherein the patient-specific jig conforms to the modeled path of the fixation element. In a further aspect, the method can include generating a virtual model of the bony anatomy based on the imaging data for the correction of the anatomical relationships, virtually simulating positioning of the fixation element using the virtual model with the corrected anatomical relationships, generating a design of the fixation element based on the virtual simulation, and design the patient-specific jig based on the design of the fixation element. The patient-specific jig can be generally or substantially congruent (e.g., geometrically congruent) to the modeled path of the fixation element. The virtual model can be a three-dimensional model (e.g., CAD model) that includes material properties, surface properties, etc.

In another aspect, a method for manufacturing a patient-specific jig can include simulating manufacturing of the patient-specific jig using one or more virtual three-dimensional models, identifying one or more fixation element design criteria based on a patient's anatomy and the simulation of the manufacturing of the patient-specific jig, and generating a manufacturing plan according to the identified one or more fixation element design criteria. In these and other aspects, for individual ones of the one or more fixation elements, the fixation element design criteria can include a surface finish, a mechanical, a biocompatibility, a target service life, and/or any other suitable design criteria.

In a further aspect, a method for manufacturing a patient-specific jig can include comparing a design for the patient-specific jig to one or more reference jig designs, selecting a set of the reference jig designs identified as similar to the design for the patient-specific jig, and generating a manufacturing plan for producing the patient-specific jig using a three-dimensional production machine based on manufacturing parameters associated with the set of the reference jig designs. In these and other aspects, a method for manufacturing a patient-specific jig can include accessing a patient-specific surgical plan including data associated with a usage of a fixation element for the patient, and design the patient-specific jig based at least partially on the patient-specific surgical plans.

The foregoing aspects, and other features and advantages of the invention, will be apparent from the following description of aspects of the invention, the accompanying drawings, and the claims.

BRIEF DESCRIPTION OF THE DRAWINGS

Details of one or more implementations of the subject matter of the invention are set forth in the accompanying drawings briefly described below and the related description set forth herein. Other objects, features, aspects, and advantages will become apparent from the description, the drawings, and the claims. Note that the relative dimensions of the drawings may not be drawn to scale. Like reference numbers and designations in the various drawings indicate like elements.

DETAILED DESCRIPTION

Aspects of the present invention and their advantages may be understood by referring to the figures and the following description. The descriptions and features disclosed herein can be applied to various devices, systems, software, and methods for operative procedures and operative settings. Although aspects and examples described in the figures and in the description below refer to a patient-specific jig, the term "jig" as used herein is interchangeable with the terms "template," "guide" and "pattern." Similarly, the aspects and examples described in the figures and in the description below refer to a fixation rod or rod, but such aspects and examples also generally apply to any form of a longitudinal fixation element. Also, the aspects and examples described in the figures and in the description below refer to pedicle screws or screws, but such aspects and examples also generally apply to any form of a bone anchor.

In an aspect of the present invention, a patient-specific jig, or template, is provided that can be used during surgery to confirm that a contoured longitudinal fixation element, such as a fixation rod, conforms to predetermined parameters of a patient-specific pre-operative plan.

Figure 1A:
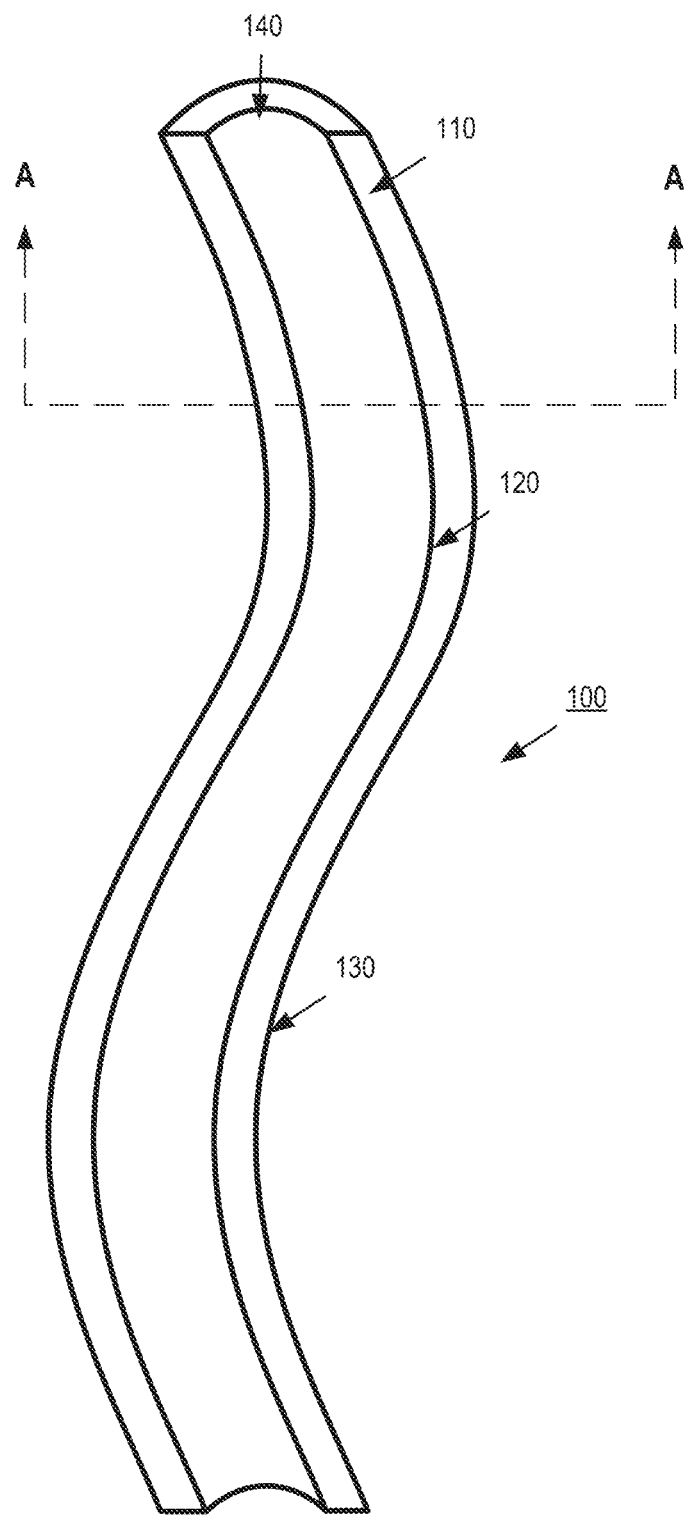
FIG. 1A is a diagram of an elongated patient-specific jig for confirmation of a fixation rod contour according to an aspect of the invention.

FIG. 1A depicts such a patient-specific jig 100 that is used during surgery to confirm that a contoured fixation rod conforms to predetermined parameters of a patient-specific pre-operative plan according to an aspect. As seen in FIG. 1A, patient-specific jig 100 includes a jig body 130 that has a top end 140 and a bottom end 150 provided at opposite ends of a longitudinal axis of jig body 130. Jig body 130 shown in FIG. 1A is seen to be formed in an elongated tubular, or partial tubular, shape but can be formed in other shapes as will be discussed further below. Jig body 130 is seen to have an outer surface formed in a tubular shape and also has an inner contour guide 120 disposed in a front surface 110 of jig body 130. Inner contour guide 120 has a contoured shape formed in three dimensions. Specifically, inner contour guide 120 is embedded in front surface 120 of jig body 130 and has a shaped cross-section in the form of a semicircle although other shapes of the cross-section are possible. The edges of inner contour guide 120 are formed in a contoured curve along the longitudinal axes of front surface 110. The contoured curve of inner contour guide 120 shown in FIG. 1A is in the form of an undulating curve but can be in the form of any contoured curve from a simple curve to a complex curve composed of many curve sections.

Figure 1B:
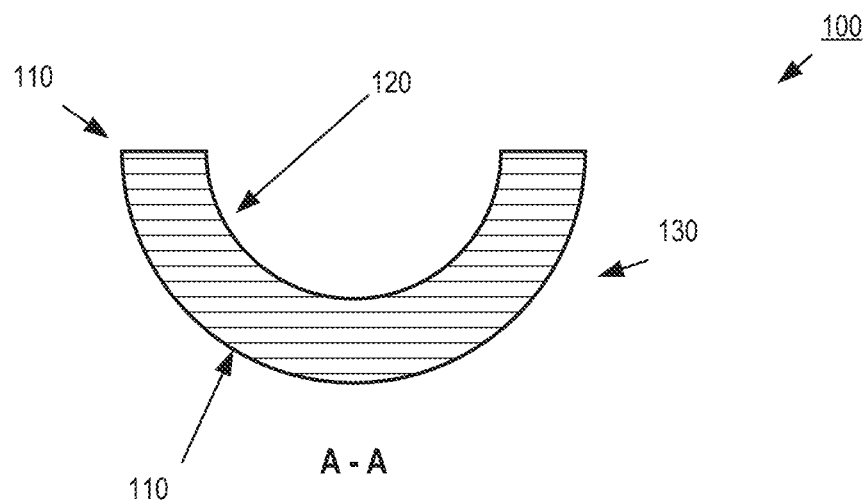
FIG. 1B is a semi-circular cross-section of the elongated patient-specific jig of FIG. 1A according to an aspect of the invention.
Figure 1C:
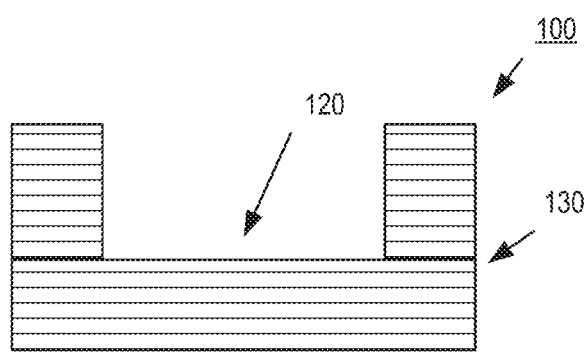
FIG. 1C is an alternative rectangular cross-section of the elongated patient-specific jig of FIG. 1A according to an aspect of the invention.
Figure 1D:
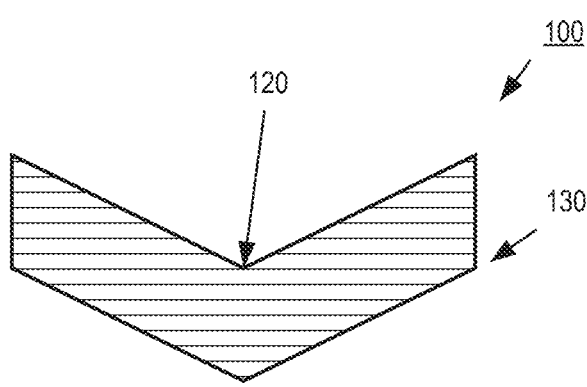
FIG. 1D is an alternative chevron cross-section of the elongated patient-specific jig of FIG. 1A according to an aspect of the invention.

Front surface 110 has a width that may be a uniform width of jig body 130. Patient-specific jig 100 has an outer back surface that is disposed opposite of front surface 110 by a uniform width. The shape of patient-specific jig 100 is such that a longitudinal fixation element, such as a fixation rod, can be placed within or against inner contour guide 120 to confirm physically and visually whether or not the fixation rod is bent and contoured correctly according to a patient-specific preoperative plan. The contoured curve of inner contour guide 120 conforms to patient-specific geometric parameters, such as geometric parameters associated with a desired curve along one or more of a patient's spine segments according to a patient-specific preoperative plan generated or initiated by a surgeon. A cross-section A-A of FIG. 1A is shown in FIGS. 1B, 1C and 1D as discussed in more detail below. Patient-specific jig 100 may be comprised of one or more types of a medical grade material such as a metal alloy, a plastic material, stainless steel, titanium, cobalt chromium, or other known types of medical grade material.

Turning to FIGS. 1B through 1D, three different example cross-section A-A shapes are shown for patient-specific jig 100. As seen in FIG. 1B, the cross section of inner contour guide 120 is shaped in the form of a semicircle. The outer surface of jig body 130 also has a semicircle shape that is separated from inner contour guide 120 by a width of front surface 110 which thereby gives patient-specific jig 100 a tubular form. As mentioned above, jig body 130 can have other formed shapes. FIG. 1C depicts patient-specific jig 100 having a rectangular right-angle form wherein a cross-section of inner contour guide 120 is formed by right angles creating three sides of a rectangle. The outer surface of jig body 130 has a similar shape and is separated from inner contour guide 120 by a width of front surface 110 thereby resulting in the cross-section of patient-specific jig 100 having a right-angle rectangular shape. FIG. 1D depicts patient-specific jig 100 having a chevron (V-shaped) form wherein a cross-section of inner contour guide 120 is formed by two intersecting lines as a chevron. The outer surface of jig body 130 has a similar shape and is separated from inner contour guide 120 by a width such that the cross-section of patient-specific jig 100 has a chevron shape.

Figure 2A:
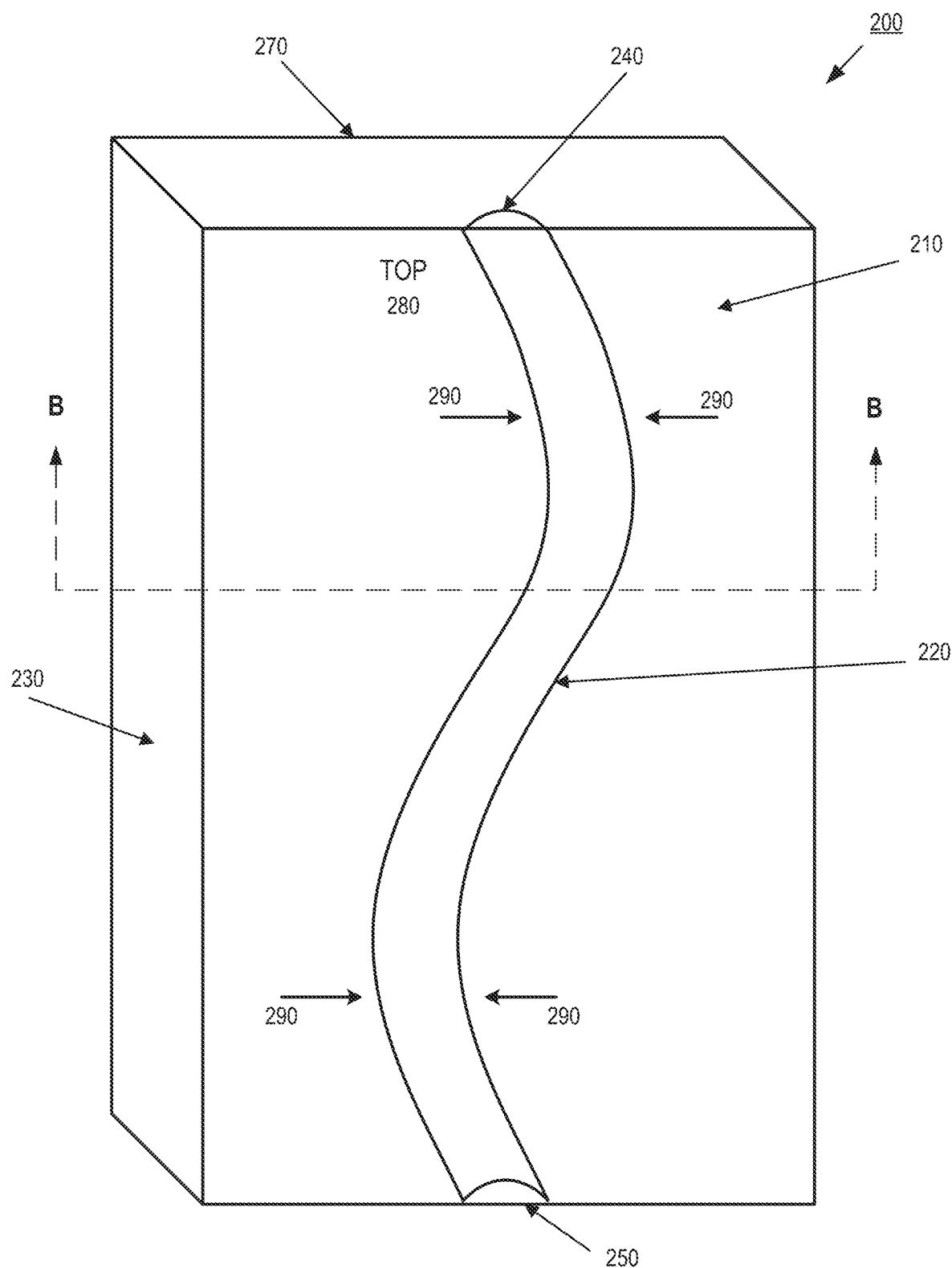
FIG. 2A is a diagram of a planar patient-specific jig for confirmation of a longitudinal fixation element contour according to an aspect of the invention.

FIG. 2A depicts an alternate form of a patient-specific jig 200 that is used during surgery to confirm that a contoured fixation rod conforms to predetermined parameters of a patient-specific pre-operative plan according to an aspect. As seen in FIG. 2A, patient-specific jig 200 includes a jig body 230 that is formed in a three-dimensional block shape. Jig body 230 has a top end 240 and a bottom end 250 provided at opposite ends of a longitudinal axis of jig body 230. Jig body 230 has an inner contour guide 220 disposed in a front surface 210 of jig body 230. Inner contour guide 220 has a contoured shape formed in three dimensions. Specifically, inner contour guide 220 is embedded in front surface 220 of jig body 230 and inner contour guide 220 has a shaped cross-section in the form of a semicircle although other shapes of the cross-section are possible. The edges of inner contour guide 220 are formed in a contoured curve along the longitudinal axes of front surface 210. The contoured curve of inner contour guide 220 shown in FIG. 2A is in the form of an undulating curve but can be in the form of any contoured curve from a simple curve to a complex curve composed of many curve sections.

The relative depth, height, and width dimensions of the three-dimensional block form of jig body 230 shown in FIG. 2A are an example, and the form of jig body 230 may have other relative dimensions. Jig body 230 has a back surface 270 that is disposed opposite of front surface 210 by the depth dimension of jig body 230. Front surface 210 and back surface 270 are planar so that patient-specific jig 100 may positioned in a stable manner on a flat surface for use in an operative setting. The contoured curve of inner contour guide 220 conforms to patient-specific geometric parameters, such as geometric parameters associated with a desired curve along one or more of a patient's spine segments according to a patient-specific preoperative plan generated or initiated by a surgeon. A top indicator 280 is provided on front surface 210 in order to assist with establishing the correct orientation of patient-specific jig 200 relative to a fixation rod for confirming that the contour of the fixation rod conforms to the contoured curve of inner contour guide 220 of patient-specific jig 200. In this manner, patient-specific jig 200 is shaped and designed such that a fixation rod can be placed within or against inner contour guide 220 to confirm physically and visually whether or not the fixation rod is bent and contoured correctly according to a patient-specific preoperative plan. If the fixation element, such as a fixation rod, is not bent and contoured correctly, the surgeon may use one or more tools to bend and/or contour the fixation element until it conforms with inner contour guide 220.

In addition, screw position indicators 290 are provided on front surface 210 to indicate where bone anchors such as pedicle screws, will be positioned along a longitudinal fixation element such as a fixation rod when the fixation rod is affixed to one or more bony structures of a patient's spine in an operative setting according to a patient-specific pre-operative plan. In this manner, a surgeon may place a fixation rod on or against inner contour guide 220 of patient-specific jig 200 with a correct orientation and alignment and then may optionally mark the fixation rod at positions relative to screw position indicators 290 in order to assist the surgeon with fixation of the fixation rod to the associated bony structures of a patient's spine. Such markings on the fixation rod may be made by the surgeon or medical professional with a surgical grade marker or laser device, or other known acceptable marking device. Patient-specific jig 200 may be comprised of one or more types of a medical grade material such as a metal alloy, a plastic material, stainless steel, titanium, cobalt chromium, or other known types of medical grade material. A cross-section B-B of FIG. 2A is shown in FIGS. 2B, 2C and 2D as discussed in more detail below.

Figure 2B:
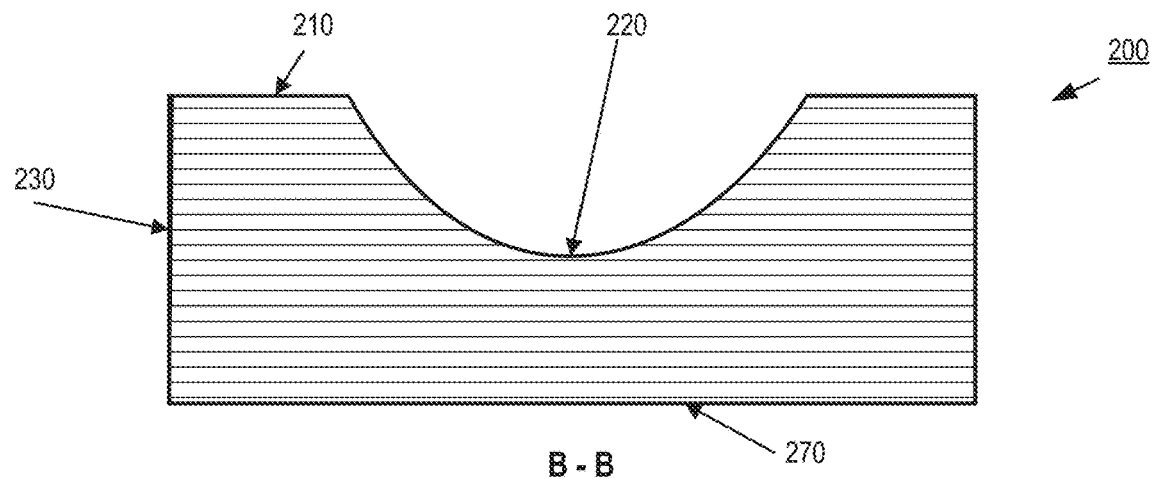
FIG. 2B is a cross-section of the planar patient-specific jig of FIG. 2A in which the inner guide has a semi-circular shape according to an aspect of the invention.
Figure 2C:
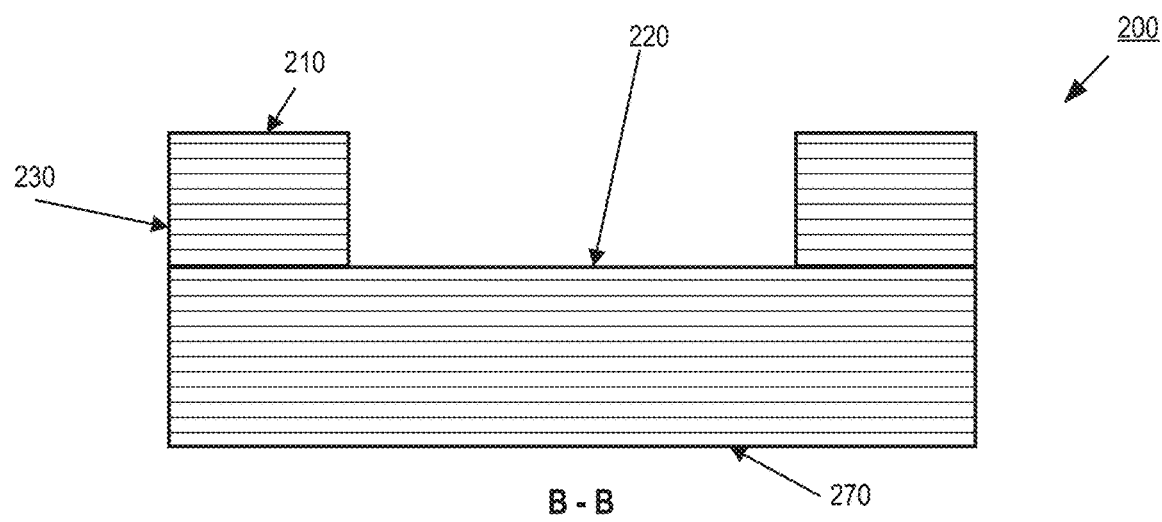
FIG. 2C is a cross-section of the planar patient-specific jig of FIG. 2A in which the inner guide has a rectangular shape according to an aspect of the invention.
Figure 2D:
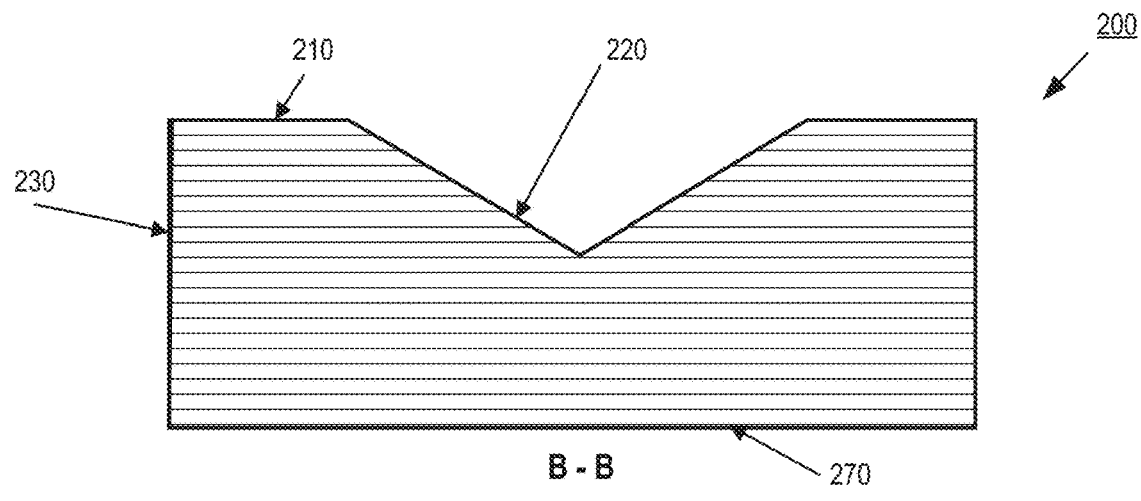
FIG. 2D is a cross-section of the planar patient-specific jig of FIG. 2A in which the inner guide has a chevron shape according to an aspect of the invention.

Turning to FIGS. 2B, 2C and 2D, three different example cross-section B-B shapes are shown for patient-specific jig 200 for FIG. 2A. As seen in FIG. 2B, the cross section of inner contour guide 220 is shaped in the form of a semicircle. The outer surface of jig body 230 is formed in a right-angled rectangular shape such that back surface 270 is planar. FIG. 2C depicts patient-specific jig 200 in which a cross-section of inner contour guide 220 has a right-angled rectangular form. The outer surface of jig body 230 is formed in a right-angled rectangular shape such that back surface 270 is planar. FIG. 2D depicts patient-specific jig 200 wherein a cross-section of inner contour guide 220 is formed by two intersecting lines as a chevron. The outer surface of jig body 230 is formed in a right-angled rectangular shape such that back surface 270 is planar.

Figure 3A:
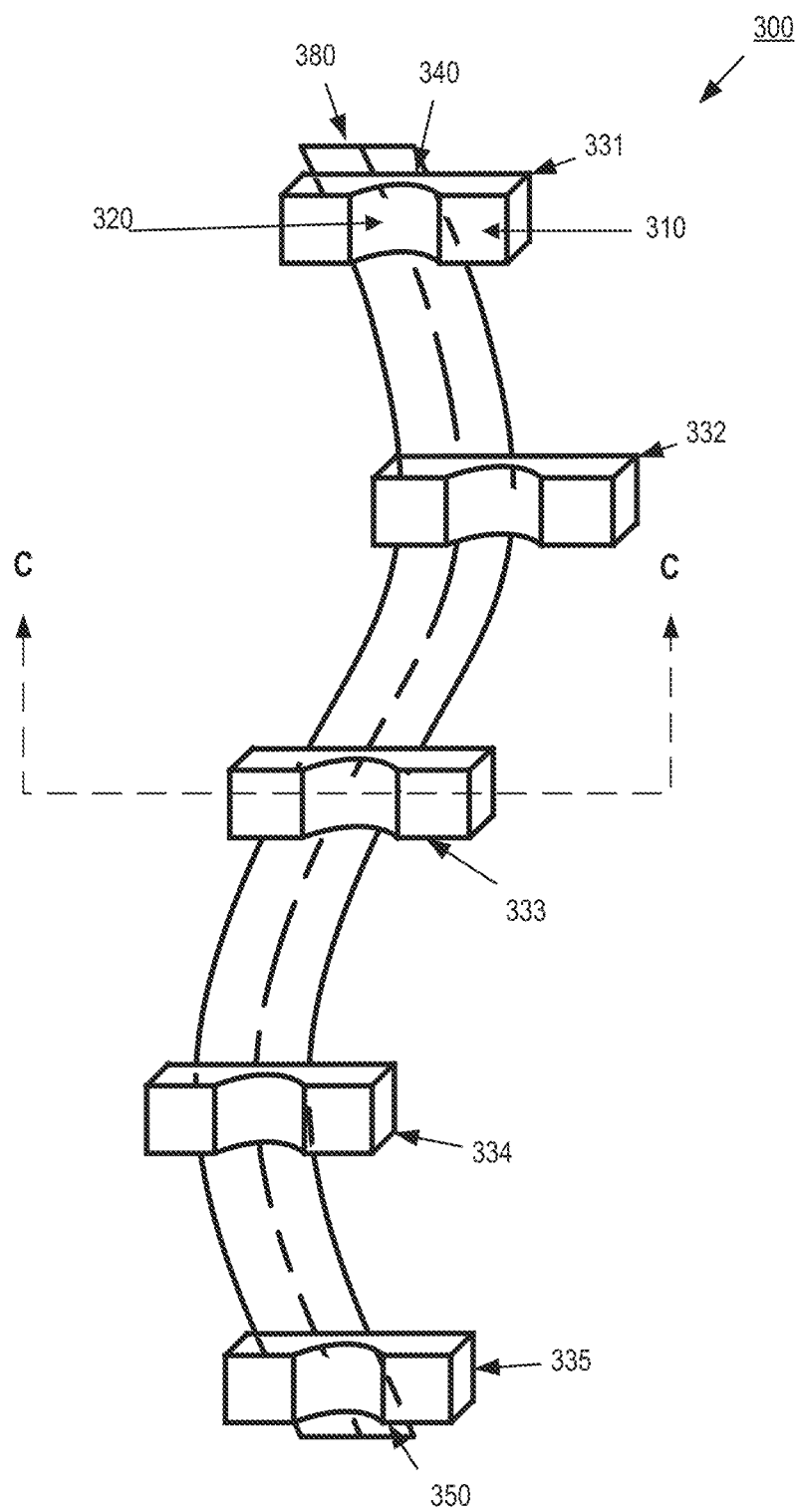
FIG. 3A is a diagram of a segmented patient-specific jig for confirmation of a fixation rod contour according to an aspect of the invention.

FIG. 3A depicts an alternative form of a patient-specific jig for use during surgery to confirm that a bent and contoured fixation rod conforms to predetermined parameters of a patient-specific pre-operative plan according to an aspect. As seen in FIG. 3A, patient-specific jig 300 is comprised of a plurality of jig body segments 331, 332, 333, 334 and 335 which are all connected to a contoured rigid member 380 which has a top end 340 and a bottom end 350. There are five jig body segments shown in FIG. 3A, but any number of jig body segments could be used to accommodate geometric parameters of a patient-specific preoperative plan. Contoured rigid member 380 is positioned along a longitudinal axis of patient-specific jig 300 and is formed in the shape of a contoured curve along the longitudinal axis that conforms to a set of patient-specific parameters. The contoured curve of contoured rigid member 380 is in the form of an undulating curve but can be in the form of any contoured curve from a simple curve to a complex curve composed of many curve sections. A back surface of each of jig body segments 331, 332, 333, 334 and 335 is connected to a surface of contoured rigid member 380, so that jig body segments 331, 332, 333, 334 and 335 are permanently or detachably attached to contoured rigid member 380. Jig body segments 331, 332, 333, 334 and 335 may be attached so as to be distributed evenly along contoured rigid member 380 or may be positioned such that they are distributed on any other pattern.

Jig body segments 331, 332, 333, 334 and 335 are shown in FIG. 3A as all being of the same shape and size; however, it should be appreciated that the jig body segments may be of different shapes, dimensions and even materials. For the sake of brevity, only jig body segment 331 will described in detail here. Jig body segment 331 is seen to have an inner contour guide 320 disposed in a front surface 310 of jig body segment 331. Specifically, inner contour guide 320 is embedded in front surface 310 of jig body segment 331 and has a shaped cross-section in the form of a semicircle although other cross-section shapes are possible.

Figure 3B:
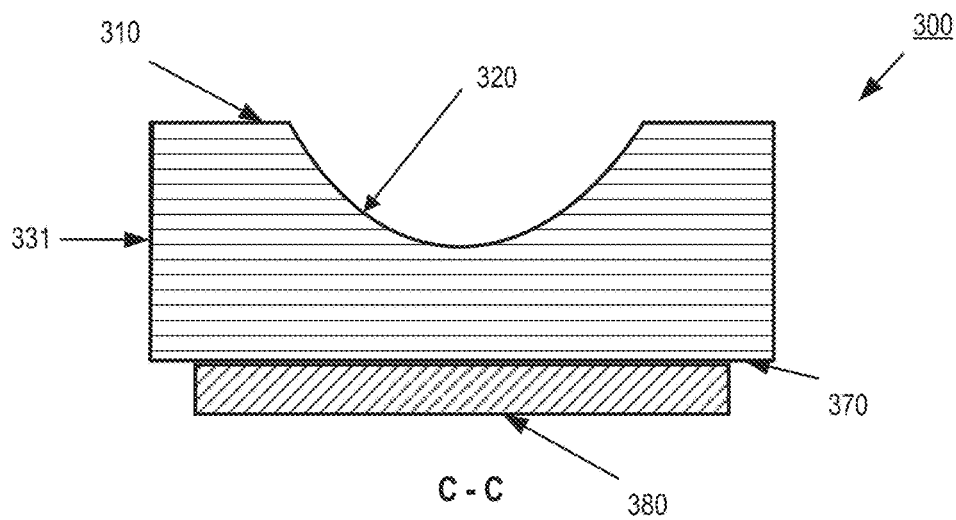
FIG. 3B is a cross-section of the segmented patient-specific jig of FIG. 3A in which the inner guide has a semi-circular shape according to an aspect of the invention.
Figure 3C:
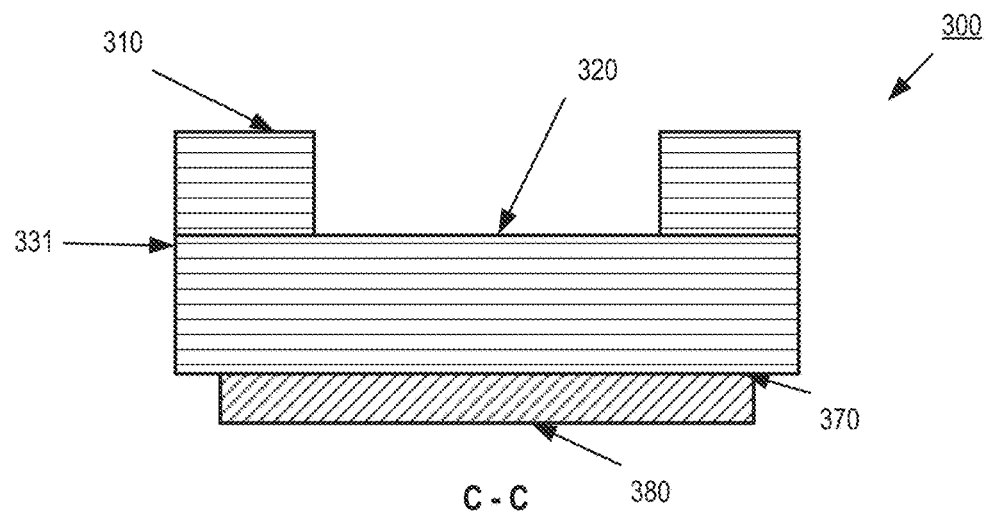
FIG. 3C is a cross-section of the segmented patient-specific jig of FIG. 3A in which the inner guide has a rectangular shape according to an aspect of the invention.
Figure 3D:
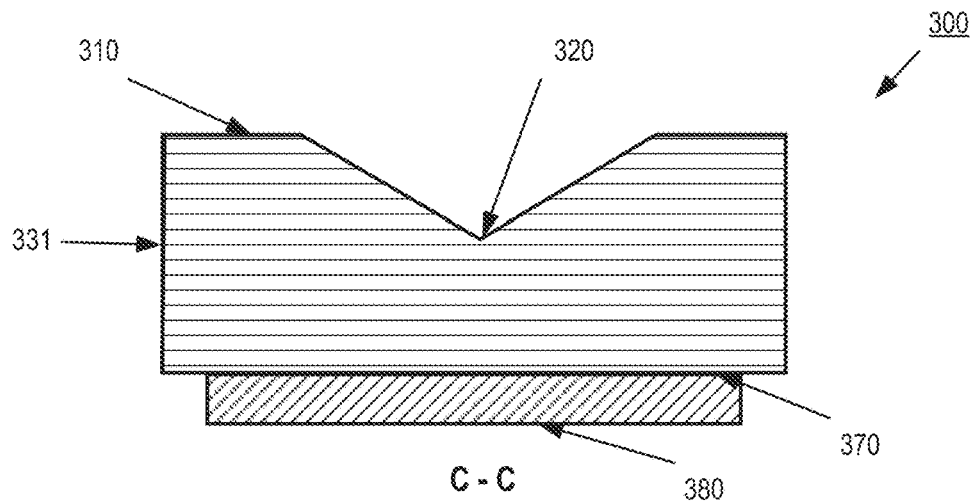
FIG. 3D is a cross-section of the segmented patient-specific jig of FIG. 3A in which the inner guide has a chevron shape according to an aspect of the invention.

The shape of patient-specific jig 300 is such that a fixation rod can be placed within or against the inner contour guides 320 of jig body segments 331, 332, 333, 334 and 335, collectively, to confirm physically and visually whether or not the fixation rod is bent and contoured correctly according to a patient-specific preoperative plan. The contoured curve of contoured rigid member 380 of patient-specific jig 300 conforms to patient-specific geometric parameters, such as geometric parameters associated with a desired curve along one or more of a patient's spine segments according to a patient-specific preoperative plan generated, initiated, or approved by a surgeon. A cross-section C-C of FIG. 3A is shown in FIGS. 3B, 3C and 3D as discussed in more detail below. Patient-specific jig 300 may be comprised of one or more types of a medical grade material such as a metal alloy, a plastic material, stainless steel, titanium, cobalt chromium, or other known types of medical grade material. The use of jig body segments to form patient-specific jig 300 can result in optimal saving of material, in comparison to a solid rectangular block shape for a single continuous jig body such as jig body 230 of FIG. 2A, for example.

Turning to FIGS. 3B through 3D, three different example cross-section C-C shapes are shown for patient-specific jig 300. As seen in FIG. 3B, the cross section of inner contour guide 320 of the jig segment body is shaped in the form of a semicircle. The outer surface of the jig segment body is formed in a right-angled rectangular shape such that a back surface 370 of the jig segment body is planar. Back surface 370 of the jig segment body is attached to a surface of contoured rigid member 380. FIG. 3C depicts patient-specific jig 300 in which the cross section of inner contour guide 320 of the jig segment body is shaped in the form of a right-angled rectangular shape. The outer surface of the jig segment body is also formed in a right-angled rectangular shape such that a back surface 370 of the jig segment body is planar. Back surface 370 of the jig segment body is attached to a surface of contoured rigid member 380. FIG. 3D depicts patient-specific jig 300 in which the cross section of inner contour guide 320 of the jig segment body is formed by two intersecting lines in the shape of a chevron (V-shaped). The outer surface of the jig segment body is also formed in a right-angled rectangular shape such that a back surface 370 of the jig segment body is planar. Back surface 370 of the jig segment body is attached to a surface of contoured rigid member 380.

As described in greater detail below, the patient-specific jig 100 of FIGS. 1A-1D, the patient-specific jig 200 of FIGS. 2A-2D, the patient-specific jig 300 of FIGS. 3A-3D, and/or any other patient-specific jig configured in accordance with embodiments of the present technology can be designed, at least partially, using one or more virtual models. For example, the virtual models can simulate a corrected anatomical configuration of the patient's anatomy, model a path or configuration of one or more fixation elements (e.g., virtual fixation elements) to achieve the corrected anatomical configuration, and design the patient-specific jig to have a contour guide (e.g., the contour guide 120, the contour guide 220, the contour guide 330) this generally or substantially congruent and/or aligned with the modeled path of one or more of the fixation elements.

Figure 4A:
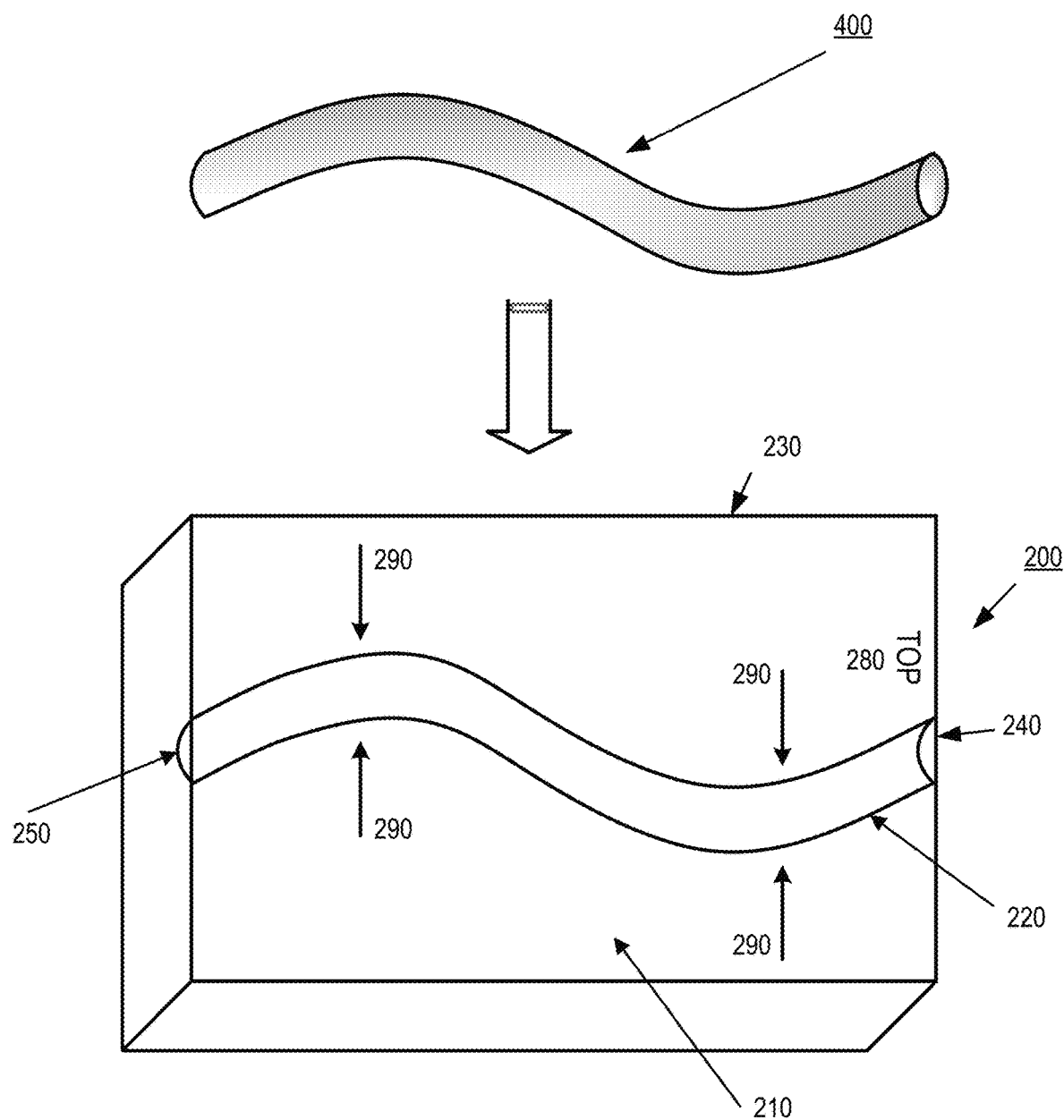
FIGS. 4A and 4B are functional diagrams depicting the use of a patient-specific jig for confirmation of a longitudinal fixation element contour according to an aspect of the invention.
Figure 4B:
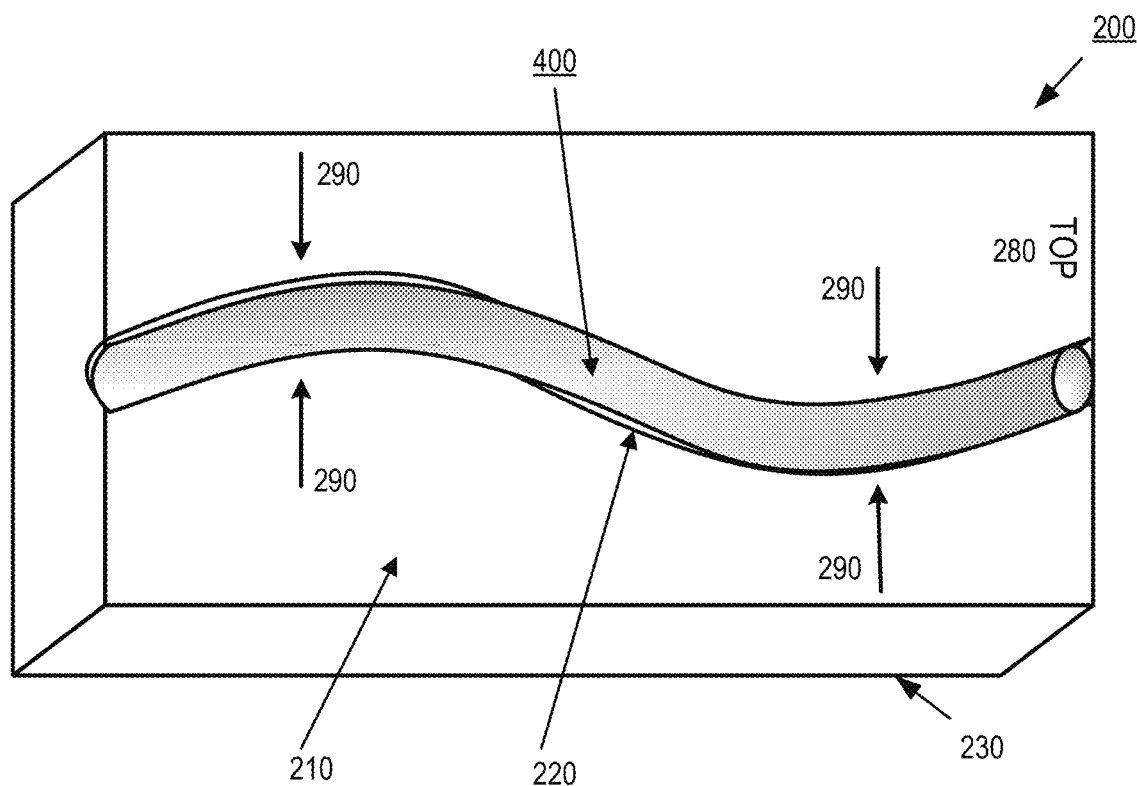

FIGS. 4A and 4B are functional diagrams depicting the use of a patient-specific jig for confirmation of a correct fixation rod contour according to an aspect of the invention. In FIG. 4A, a fixation rod 400 is shown that is about to be applied into the inner contour guide 220 of patient-specific jig 200 in order to confirm that fixation rod 400 has a contour that conforms to a set of patient-specific parameters. Patient-specific jig 200 is used here as an example, but a patient-specific jig, template or guide having other shapes and dimensions may also be used, as described above with regard to FIGS. 1A to 3D. The details of patient-specific jig 200 are not repeated here for the sake of brevity and the description provided above in association with FIGS. 2A to 2D may be referred to for such details. As seen in FIG. 4A, patient-specific jig 200 is positioned and oriented for use, such as being placed flat on a flat surface provided in an operative setting with front surface 210 and inner contour guide 220 facing upwards. Patient-specific jig 200 is designed and manufactured specifically for the patient that is the subject of the operative procedure.

A medical professional, such as a surgeon, may use one or more tools to bend and/or contour a fixation rod (fixation rod 400) during an operative procedure in order to achieve a desired contour of the fixation rod according to patient-specific preoperative plan. The surgeon then orients and positions fixation rod 400 to be moved into place in or against inner contour guide 220 of patient-specific jig 200, as indicated by the downward arrow. In FIG. 4B, fixation rod 400 is now in place within inner contour guide 220 of patient-specific jig 200. A visual inspection of the physical fit of fixation rod 400 within or against inner contour guide 220 is used by the surgeon to confirm that the contour of fixation rod 400 conforms to the patient-specific preoperative plan. There may be some spatial gap between the outer surface of fixation rod 400 and the edges of inner contour guide 220, but the contour of fixation rod may still be in conformance if the spatial gap is within an acceptable dimensional tolerance. Otherwise, if fixation rod 400 clearly does not physically fit within or against inner contour guide 220 or if a spatial gap between the outer surface of fixation rod 400 and the edges of inner contour guide 220 are not within an acceptable dimensional tolerance then fixation rod 400 does not conform to the patient-specific preoperative plan. In such a situation, the surgeon may continue to use one or more tools to further bend and/or contour fixation rod 400 until it does conform with inner contour guide 220 of patient-specific jig 200. Once the fixation rod 400 is in conformance, the surgeon may optionally mark fixation rod 400 at positions relative to screw position indicators 290 in order to assist the surgeon with alignment and fixation of fixation rod 400 to associated bony structures of the patient's spine.

Figure 5:
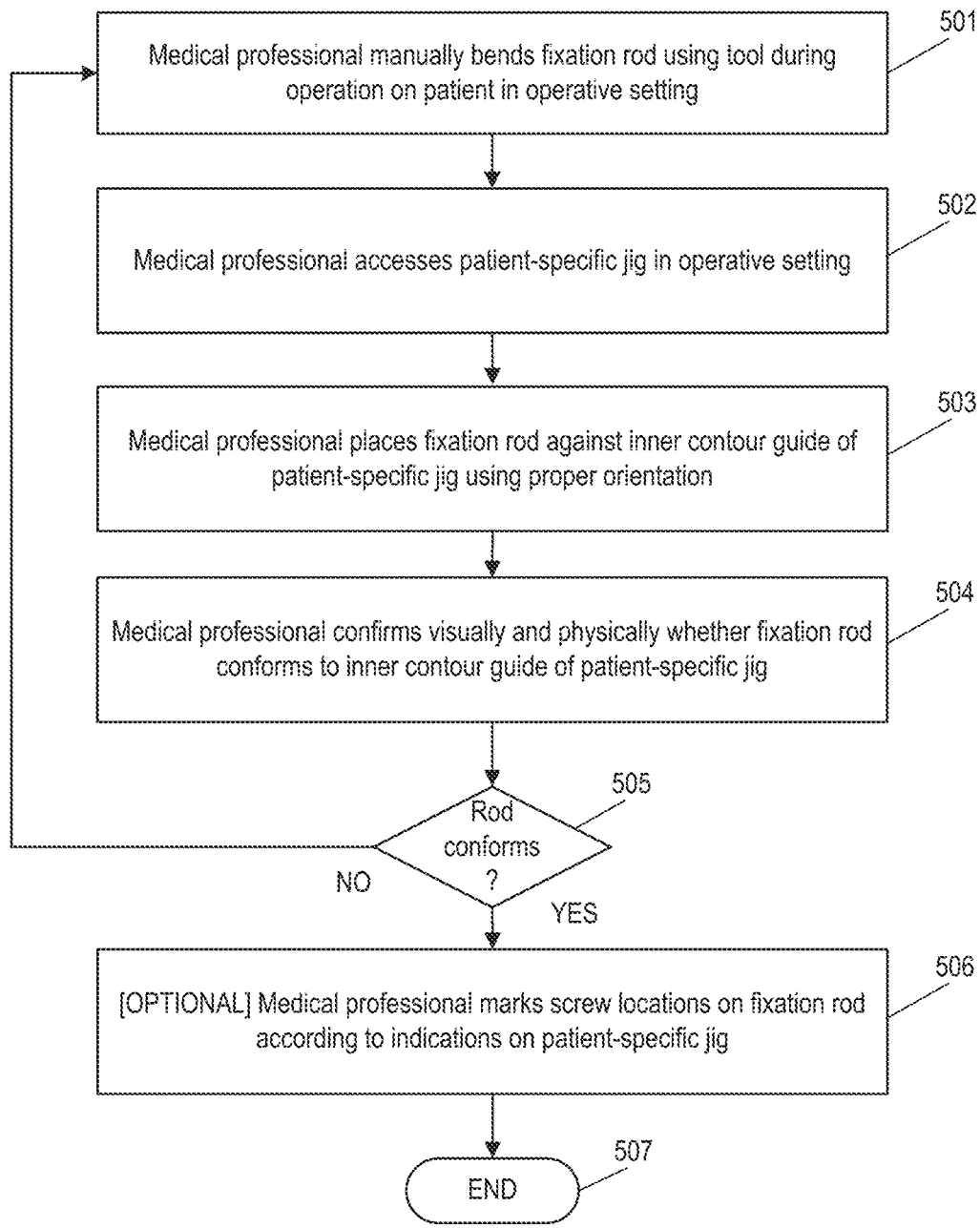
FIG. 5 is a flowchart depicting the use of a patient-specific jig for confirmation of a longitudinal fixation element contour according to an aspect of the invention.

FIG. 5 is a flowchart depicting the use of a patient-specific jig for confirmation of a correct fixation rod contour according to an aspect of the invention. In step 501, a medical professional manually bends a fixation rod using a tool during an operation on a patient in an operative setting. The medical professional, who may be a surgeon, uses one or more tools to bend and/or contour the fixation rod during an operative procedure in order to achieve a desired contour of the fixation rod according to patient-specific preoperative plan. Next, in step 502, the medical professional accesses a patient-specific jig in the operative setting. The patient-specific jig may be positioned and oriented for use, such as being placed on a flat surface provided in an operative setting with an inner contour guide of the patient-specific jig facing upwards. In step 503, the medical professional places the fixation rod against the inner contour guide of the patient-specific jig using proper orientation. At this point, the medical professional confirms visually and physically in step 504 whether the contour of the fixation rod conforms to the inner contour guide of the patient-specific jig. There may be some spatial gap between the outer surface of the fixation rod and the edges of inner contour guide, but the contour of the fixation rod may still be in conformance if the spatial gap is within an acceptable dimensional tolerance. A determination is made at step 505 whether the contour of the fixation rod conforms to the inner contour guide. If it does, then the medical professional may optionally mark screw locations on the fixation rod according to screw position indications on the patient-specific jig and the process ends at step 507. Otherwise, if at step 505 it is determined that the contour of the fixation rod does not conform to the inner contour guide, the process reverts back to step 501 at which the medical professional again bends and/or contours the fixation rod in an a further attempt to achieve conformance with the inner contour guide. For example, if the fixation rod clearly does not physically fit within or against the inner contour guide or if a spatial gap between the outer surface of the fixation rod and the edges of inner contour guide are not within an acceptable dimensional tolerance then the fixation rod does not conform to the inner contour guide and therefore does not conform to the patient-specific preoperative plan.

Figure 6:
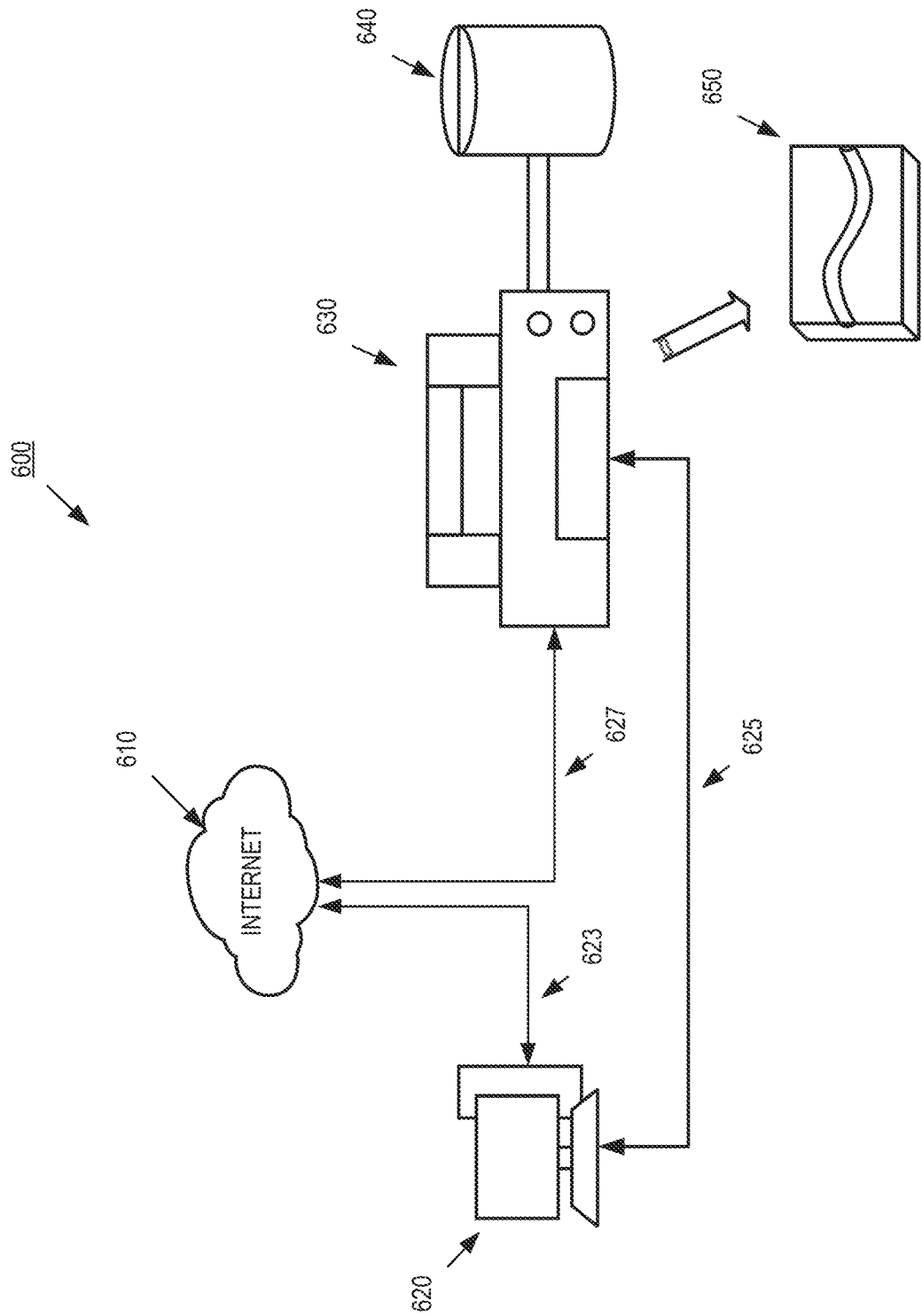
FIG. 6 is a functional diagram depicting the manufacture of a patient-specific jig for confirmation of a longitudinal fixation element contour according to an aspect of the invention.

FIG. 6 is a functional diagram depicting the manufacture of a patient-specific jig for confirmation of a fixation rod contour according to an aspect of the invention. FIG. 6 shows a number of devices in a networked environment that operate in a coordinated manner to manufacture a patient-specific jig. The networked environment of FIG. 6 may be a sterile or a non-sterile environment. In FIG. 6, a computing device 620 is provided which may be a general-purpose computer or a specific or customized computer utilized for manufacturing a patient-specific jig, such as a patient-specific implant design system. A descriptive example of computing device 620 is provided in more detail below with regard to FIG. 11. Returning to FIG. 6, a three-dimensional production machine 630 is also provided and has a communication connection 625, either direct or via a network, with computing device 620. Three-dimensional production machine 630 may be an additive manufacturing machine such as a three-dimensional printer or other form of three-dimensional material deposition machine. In the alternative, three-dimensional production machine 630 may be a subtractive manufacturing machine such as a three-dimensional production computer numerical control (CNC) machine that removes material from an initial solid piece of material to manufacture a shaped three-dimensional object. Computing device 620 and three-dimensional production machine 630 are also connected to the internet via communication connections 623 and 627, respectively. Three-dimensional production machine 630 has a material supply system 640 that supplies production material to three-dimensional production machine 630 for producing patient-specific jig 650. The production material supplied by material supply system 640 may be one or more types of a medical grade material such as a metal alloy, a plastic material, stainless steel, titanium, cobalt chromium, or other known types of medical grade material.

Computing device 620 can access a data file either from a memory provided in computing device 620 or from a remote server via its internet connection 623, wherein the data file contains patient-specific geometric parameters associated with a patient-specific preoperative plan. For example, the patient-specific geometric parameters may define a contoured curve for a fixation rod that is to be used during an operative procedure for attachment to a plurality of a patient's spine segments in accordance with a patient-specific preoperative plan. As described previously, and in greater detail below, in some embodiments the fixation rod can be a virtual or simulated fixation rod, and the patient-specific geometric parameters (e.g., the contoured curve) of the virtual fixation rod can be generated by one or more virtual models. Computing device 620 can also access a data file from a patient-specific implant design system via its internet connection 623, wherein the patient-specific implant design system may be operated by a third-party company for example. Computing device 620 then converts the patient-specific geometric parameters into a machine data set that can be used by three-dimensional production machine 630 to produce patient-specific jig 650. In this regard, computing device 620 may utilize a manufacturing software system or a machine-specific software driver unit to convert the patient-specific geometric parameters into a machine data set. As described in greater detail below, the patient-specific geometric parameters for the patient-specific jig 650 can be generated based at least partially on one or more virtual models of the patient's native and/or corrected anatomy. Computing device 620 sends the machine data set to three-dimensional production machine 630 upon which three-dimensional production machine 630 produces patient-specific jig 650 in accordance with the machine data set. For example, producing the patient-specific jig 650 in accordance with the machine data set can include producing the patient-specific jig 650 to include a contour guide shaped generally or substantially similar to the contoured curve of the fixation rod. Computing device 620 may send the machine data set to three-dimensional production machine 630 via connection 625 or via connections 623 and 627 (through the internet).

Figure 7:
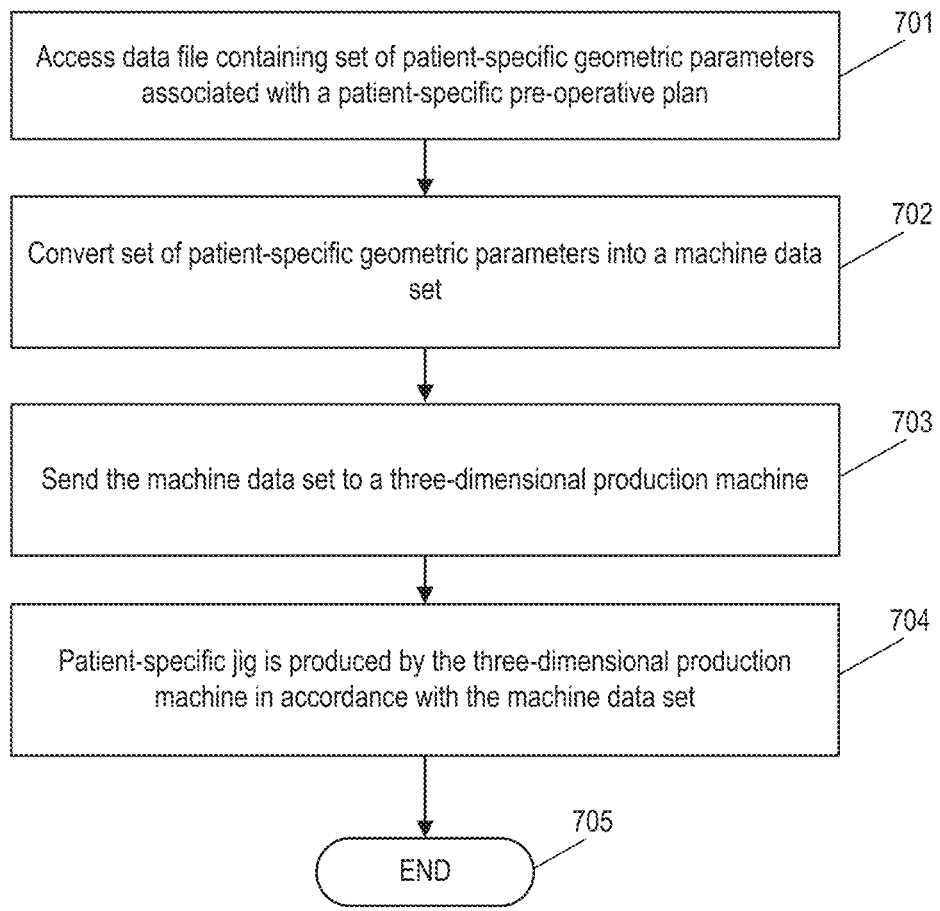
FIG. 7 is a flowchart depicting the manufacture of a patient-specific jig for confirmation of a longitudinal fixation element contour according to an aspect of the invention.

FIG. 7 is a flowchart depicting the manufacture of a patient-specific jig for confirmation of a fixation rod contour according to an aspect of the invention. In step 701, a data file is accessed wherein the data file contains a set of patient-specific geometric parameters associated with a patient-specific pre-operative plan. Next, in step 702, the set of patient-specific geometric parameters are converted into a machine data set. In step 703, the machine data set is sent to a three-dimensional production machine, and then in step 704 a patient-specific jig is produced by the three-dimensional production machine in accordance with the machine data set.

Figure 8:
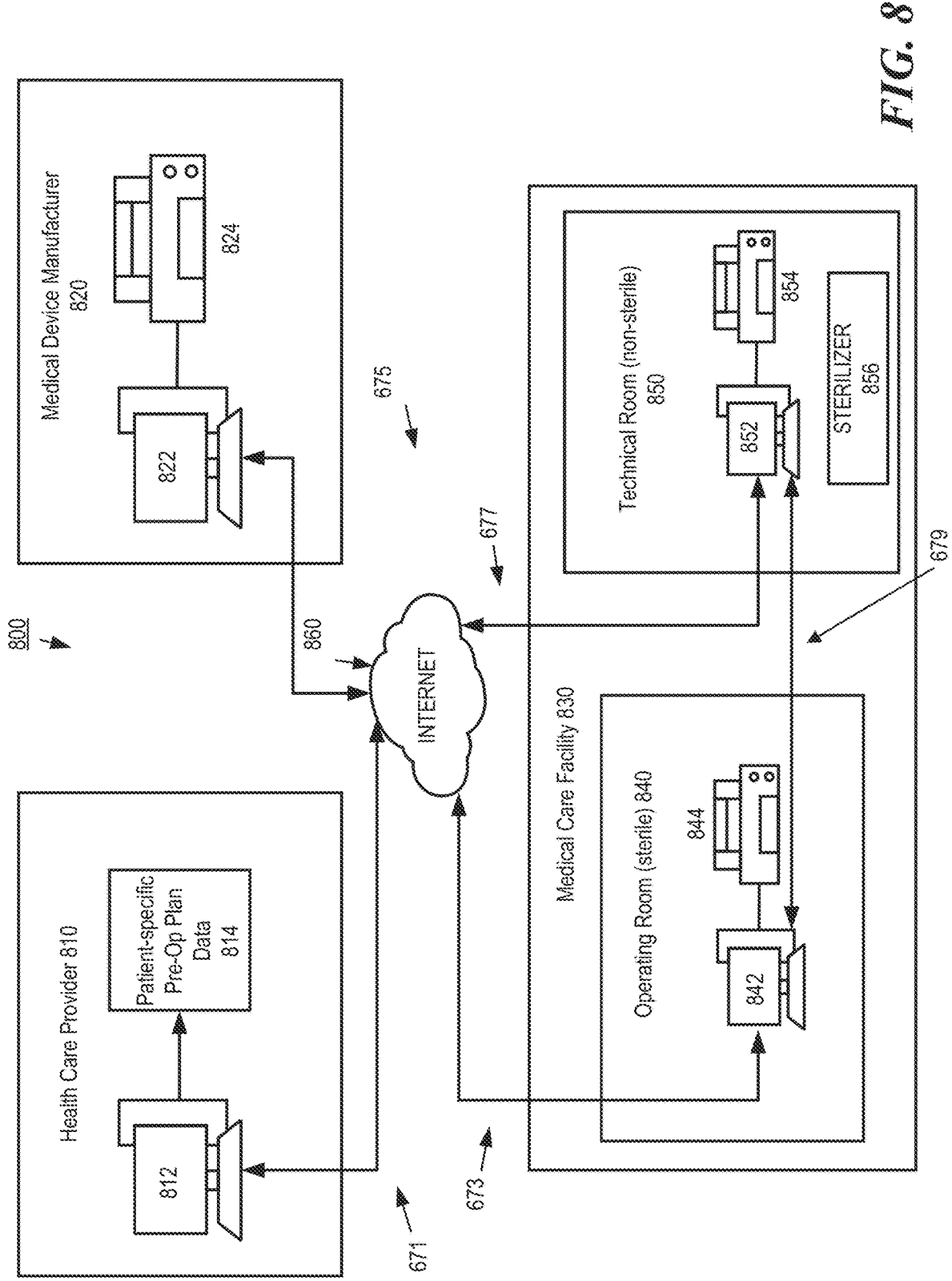
FIG. 8 is a functional diagram depicting a health care environment utilized in the manufacture of a patient-specific jig for confirmation of a longitudinal fixation element contour according to an aspect of the invention.

FIG. 8 is a functional diagram depicting a health care environment 800 utilized in the manufacture of a patient-specific jig for confirmation of a fixation rod contour according to an aspect of the invention. The health care environment of FIG. 8 includes health care provider 810, medical device manufacturer 820 and medical care facility 830 all of which are connected to each other through internet 860. Health care provider 810 includes computing device 812 which has a memory device that contains patient-specific preoperative plan data 814. Computing device 812 is similar in functionality to computing device 620 of FIG. 6 and may be a general-purpose computer or a specific or customized computer utilized for manufacturing a patient-specific jig, such as a patient-specific implant design system. A descriptive example of a computing system such as computing device 812 is provided below with regard to FIG. 11. Health care provider 810 may represent an office or facility of a doctor, surgeon, or medical group, so that a doctor, surgeon, or other medical professional can use computing device 812 to generate or initiate patient-specific preoperative plan data 814.

The data contained in patient-specific preoperative plan data 814 may include data related to a specific patient that the medical professional is treating and that will be the subject of an operative procedure such as corrective spine surgery, and may include 3D imaging data. More specifically, the patient-specific preoperative plan data 814 can include data representative of the patient's condition, anatomy, pathology (e.g., spinal pathology), medical history, preferences, and/or any other information or parameters relevant to the patient. For example, the patient-specific preoperative plan data 814 can include a patient data set include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like.

In addition to personal information of the patient, patient-specific preoperative plan data 814 also includes patient-specific geometric parameters which may for example define a contoured curve for a fixation rod that is planned to be used in the operative procedure for attachment to a plurality of the patient's spine segments. The patient-specific geometric parameters may be associated with a pathological condition or a relative orientation of alignment of one or more of the patient's spine segments. This can include data representing one or more of the patient's age, gender, body mass index (BMI), lumbar lordosis, Cobb angle(s), pelvic incidence, disc height, segment flexibility, bone quality, rotational displacement, and/or treatment level of the spine. The medical professional may utilize software programs, systems and applications operating on computing device 812 to generate or initiate patient-specific preoperative plan data 814. For example, computing device 812 may contain a computer automated design program or system for use by a medical professional to generate patient-specific geometric parameters that define a contoured curve for a fixation rod. In other embodiments, computer automated design program or system can operate automatically or semi-autonomously, e.g., to generate the patient-specific geometric parameters based on one or more virtual models, patient data set, and/or reference patient data sets.

Computing device 812 may implement or utilize a patient-specific implant design system or program, or a surgical assistance program for use by a medical professional to generate, based at least in part on the patient-specific preoperative plan data 814, one or more patient-specific geometric parameters that define a contoured curve for a fixation rod. Such a patient-specific implant design system or program, or a surgical assistance program may be one or more of the novel embodiments, features, systems, devices, materials, methods, programs, and techniques as described in the following: (1) U.S. Publication No. 20190167435, published on Jun. 6, 2019, titled "SYSTEMS AND METHODS FOR MULTI-PLANAR ORTHOPEDIC ALIGNMENT;" (2) U.S. Publication No. 20190282367, published on Sep. 19, 2019, titled "SYSTEMS AND METHODS FOR ORTHOPEDIC IMPLANT FIXATION;" (3) U.S. Publication No. 20190321193, published on Oct. 24, 2019, titled "SYSTEMS AND METHODS FOR ORTHOPEDIC IMPLANT FIXATION;" (4) U.S. Publication No. 20200078180, published on Mar. 12, 2020, titled "SYSTEMS AND METHODS FOR ORTHOPEDIC IMPLANTS;" and (5) U.S. Publication No. 20200170802, published on Jun. 4, 2020, titled "SYSTEMS AND METHODS FOR ORTHOPEDIC IMPLANTS." All of the above-identified published patent applications are incorporated by reference herein in their entireties. The systems, methods and techniques described in the above-listed published patent applications in combination with the descriptions provided herein can be used to implement a patient-specific implant design system or program, or a surgical assistance program in order to produce a patient-specific jig. For example, as described in greater detail below, a patient-specific jig may be produced by accessing a data file containing imaging data that represents bony anatomy associated with a patient, generating one or more virtual models based, at least in part, on the imaging data, correcting anatomical relationships of the bony anatomy in a virtual space (via, e.g., a virtual model, a virtual simulation, an interactive representation of the patient's anatomy and/or anatomical relationships, etc.), modelling (e.g., with the virtual model) a path of a fixation element between a plurality of bony anatomical landmarks associated with the corrected anatomical relationships of the bony anatomy, and producing a patient-specific jig with a three-dimensional production machine, wherein the patient-specific jig conforms to or is generally or substantially congruent with the modeled path of the fixation element.

In some embodiments, correcting anatomical relationships of the bony anatomy in the virtual space includes generating multiple anatomical models of the patient. For example, the patient-specific preoperative plan data 814 can include a first model showing the patient's native (e.g., pre-operative) anatomical configuration, and a second model providing a simulation of the patient's corrected (e.g., post-operative) anatomical configuration. The second virtual model may optionally include one or more virtual implants shown as implanted at one or more target regions of the patient. Spine metrics (e.g., lumbar lordosis, Cobb angels, coronal parameters, sagittal parameters, pelvic parameters, etc.) can also be provided for both the pre-operative anatomical configuration and expected post-operative anatomical configuration.

In some embodiments, the patient-specific jig can be designed based at least partially on one or more virtual models of the patient's bony anatomy. It at least some embodiments, for example, the patient-specific jig can be design based at least partially on the second virtual model of the patient's corrected anatomical configuration. The second virtual model can optionally include one or more virtual fixation elements positioned, design, and/or modelled based at least partially on the patient's corrected anatomical configuration and/or the one or more virtual implants. The virtual fixation elements can include, for example, a modeled path between a plurality of bony anatomical landmarks associated with the corrected anatomical relationships of the virtual model of the patient's corrected bony anatomy. The one or more virtual fixation elements can be used to generate designs for one or more fixation elements, and one or more patient-specific jigs can be designed based at least partially on one or more geometric parameters associated with the generated designs for the one or more fixation elements. For example, the patient-specific jig can be designed to be generally or substantially congruent to the modeled path of the fixation element, as previously described herein.

In some embodiments, one or more virtual models (e.g., three-dimensional models) can be used to simulate manufacturing of the patient-specific jig. The one or more virtual models can be generally similar to or the same as the virtual models used to simulate the patient's native and/or corrected anatomical configuration. The computing system 812 can analyze the simulated manufacturing of the patient-specific jig and the patient's native and/or corrected anatomical configuration (using, e.g., one or more of the virtual models described previously) to identify one or more fixation element design criteria. The computing system 812 can construct and manipulate complex three-dimensional (3D) models in one or more simulations environments. Parametric modeling techniques can be used to define various parameters for different features and components of a model (e.g., implant model, anatomy model, etc.), and to define relationships between those features and components based on relationships between the various parameters. In some embodiments, the fixation element design criteria can be based at least partially on reference patient data sets. The one or more fixation element design criteria can be aspects of a design for one or more fixation elements and be associated with a desired or favorable patient outcome. For example, the computing device 812 can select one or more aspects of a design of one or more reference jig designs and/or reference fixation element designs associated with the desired or favorable patient outcome, and generate a design for one or more of the fixation elements based at least partially on the selected aspects of the reference jig designs and/or reference fixation element designs. The one or more fixation element design criteria can include, for example, a surface finish, a mechanical strength, a biocompatibility, a target service life, and/or any other suitable design criteria for one or more of the fixation elements.

In some embodiments, the patient-specific preoperative plan data 814 can based, at least in part, on previous treatment data from reference patients. For example, computing device 812 can include a treatment planning module configured to receive a selected subset of reference patient data sets and/or similar patient data sets and determine or identify treatment data from the selected subset. The patient-specific preoperative plan data 814 can include, for example, treatment procedure data (e.g., surgical procedure or intervention data) and/or medical device design data (e.g. implant design data, jig design data, fixation element design data, etc.) that are associated with favorable or desired treatment outcomes for the corresponding patient. The treatment planning module can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment procedure(s) and/or medical device design(s) based on the score (e.g., higher or highest score; lower or lowest score; score that is above, below, or at a specified threshold value). The personalized patient-specific treatment plan can be based, at least in part, on the patient-specific technologies or patient-specific selected technology described herein.

Alternatively or in combination, the treatment planning module can generate the patient-specific preoperative plan data 814 based on correlations between data sets. For example, the treatment planning module can correlate treatment procedure data and/or medical device design data from similar patients with favorable outcomes (e.g., as described previously). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated. For example, the computing system 812 can compare a design for a patient-specific jig with one more reference jig designs, select a set of reference jig designs identifies as similar to the design for the patient-specific jig, and generate a manufacturing plan for producing the patient-specific jig based on manufacturing parameters associated with the selected set of reference jig designs. As a further example, the computing system 812 can access a patient-specific surgical plan for the patient. The patient-specific surgical plan can include information associated with a usage (e.g., a position, a modeled path, one or more anatomical landmarks, etc.) of the fixation element, and the computing system 812 can design the patient-specific jig 812 based on such patient-specific surgical plan.

Alternatively or in combination, the treatment planning module can generate the patient-specific preoperative plan data 814 using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems. Alternatively, or in combination, the treatment planning module generates the patient-specific preoperative plan data 814 using one or more trained machine learning models. Various types of machine learning models, algorithms, and techniques are suitable for use with the present technology. Alternatively, or in combination, the machine learning model (e.g., a neural network or a naïve Bayes classifier) may be trained using a supervised learning method (e.g., gradient descent or stochastic gradient descent).

The patient-specific preoperative plan data 814 generated by the treatment planning module can include at least one patient-specific treatment procedure (e.g., a surgical procedure or intervention) and/or at least one patient-specific medical device (e.g., an implant or implant delivery instrument, a jig, a patient-specific jig, a fixation element, etc.). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation elements, anchors, nuts, bolts, rivets, connectors, tethers, fasteners, joint replacements, hip implants, or the like. Examples of instruments include, but are not limited to, screw guides, cannulas, ports, catheters, insertion tools, or the like. In these and other embodiments, the patient-specific medical device design can further include a design for a patient-specific jig for a medical procedure, such as a design for any of the patient-specific jigs described herein, and the design for the patient-specific jig can be based at least partially on a design for an orthopedic implant and/or a design for a delivery instrument.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). As another example, a design for a patient-specific jig can include physical properties, mechanical properties, and/or biological properties of a corresponding patient-specific jig and/or a corresponding fixation element (e.g., before, during, and/or after the patient-specific jig is used to confirm a contour of the fixation element). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. As another example, a patient-specific jig can be design for use with a standard, off-the-shelf fixation element. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In some embodiments, the computing device 812 includes or is operably coupled to a display (such as the display 1120 of FIG. 11) for outputting the treatment plan(s). The display can include a graphical user interface (GUI) for visually depicting various aspects of the treatment plan(s). For example, the display can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display can show a design for a medical device to be implanted in the patient, such as a two- or three-dimensional model of the device design, and/or other devices (e.g., patient-specific jigs or templates) that are part of the implantation procedure. The display can also show patient information, such as two- or three-dimensional images or models of the patient's anatomy where the surgical procedure is to be performed and/or where the device is to be implanted. The computing device 812 can further include one or more user input devices (such as input devices 1110 of FIG. 11) allowing the user to modify, select, approve, and/or reject the displayed treatment plan(s).

Additional details about patient-specific treatments, including virtual anatomical models and patient-specific surgical plans, can be found in PCT Application No. PCT/US21/12065, filed Jan. 4, 2021, titled "PATIENT-SPECIFIC MEDICAL PROCEDURES AND DEVICES, AND ASSOCIATED SYSTEMS AND METHODS," the entirety of which is incorporated by reference herein.

Medical device manufacturer 820 includes computing device 822 and three-dimensional machine 824. Computing device 822 has similar functionality as computing device 812 and three-dimensional machine 824 may be an additive manufacturing machine such as a three-dimensional printer or other form of three-dimensional material deposition machine. In the alternative, three-dimensional production machine 824 may be a subtractive manufacturing machine such as a three-dimensional production computer numerical control (CNC) machine that removes material from an initial solid piece of material to manufacture a shaped three-dimensional object. Computing device 822 and three-dimensional machine 824 are connected by a communication connection and, similar to the system of FIG. 6, computing device 822 may send a machine data set to three-dimensional machine 824 upon which three-dimensional machine 824 produces a patient-specific medical device (e.g., a patient-specific jig) in accordance with the machine data set. Three-dimensional machine 824 may be located in a sterile or a non-sterile location of medical device manufacturer 820.

Medical care facility 830 includes operating room 840 at least a portion of which is a sterile environment, and technical room 850 which is a non-sterile environment. Operating room 840 includes computing device 842 and three-dimensional machine 844, which are similar in functionality to computing device 822 and three-dimensional machine 824, respectively. Computing device 842 and three-dimensional machine 844 are connected by a communication connection and, similar to the system of FIG. 6, computing device 842 may send a machine data set to three-dimensional machine 844 upon which three-dimensional machine 844 produces a patient-specific jig in accordance with the machine data set.

Technical room 850, which is in a non-sterile environment, includes computing device 852 and three-dimensional machine 854 which are similar in functionality to the other computing devices and three-dimensional machines shown in FIG. 8. Computing device 852 and three-dimensional machine 854 are connected by a communication connection and, similar to the system of FIG. 6, computing device 852 may send a machine data set to three-dimensional machine 854 upon which three-dimensional machine 854 produces a patient-specific jig in accordance with the machine data set. Technical room 850 also includes sterilizer 856 which is used to sterilize a patient-specific jig produced by three-dimensional machine 854 in technical room 850 so that a sterilized patient-specific jig can be delivered to operative room 840 for use in an operative procedure on a patient associated with the sterilized patient-specific jig. Medical device manufacturer 820 may also implement and utilize a sterilizer (not shown) depending on whether three-dimensional machine 824 is located in a sterile or a non-sterile environment.

The distributed system of health care environment 800 allows a patient-specific jig to be produced in a number of locations for ultimate use in operating room 840 during an operative procedure on an associated patient. For example, a medical professional at health care provider 810, such as a surgeon or doctor, can utilize software programs, systems and applications operating on computing device 812 to generate or initiate patient-specific preoperative plan data 814 that includes patient-specific geometric parameters. The medical professional can send, or make available (with computing device 812 acting as a remote server), patient-specific preoperative plan data 814 to medical device manufacturer 820 upon which computing device 822 can access patient-specific preoperative plan data 814 and convert the patient-specific geometric parameters contained therein to a machine data set which computing device 822 sends to three-dimensional machine 824 causing three-dimensional machine 824 to produce a patient-specific jig in accordance with the machine data set. Medical device manufacturer 820 then sends the patient-specific jig to medical care facility 830 for use in an operative procedure in operating room 840 on a patient associated with the patient-specific jig.

Similarly, the medical professional can send, or make available (with computing device 812 acting as a remote server), patient-specific preoperative plan data 814 to medical care facility 830 so that a patient-specific jig can be produced in the sterile environment of operating room 840 by computing device 842 and three-dimensional machine 844 in the same manner as described above with respect to computing device 822 and three-dimensional machine 824. This process may be used when it is desired to produce the patient-specific jig immediately before an operative procedure is to be conducted on the associated patient, for example. Alternatively, it may be decided by medical care facility 830 or by a medical professional at health care provider 810 to have the patient-specific jig produced in the non-sterile environment of technical room 850. In this case, the patient-specific jig is produced in the non-sterile environment of technical room 850 by computing device 852 and three-dimensional machine 854 in the same manner as described above with respect to computing device 842 and three-dimensional machine 844. After the patient-specific jig is produced in the non-sterile environment of technical room 850, it can be sterilized by sterilizer 856 for delivery to operating room 840. This process may be used when it is desired to produce the patient-specific jig significantly in advance of an operative procedure to be conducted on the associated patient, for example.

Figure 9:
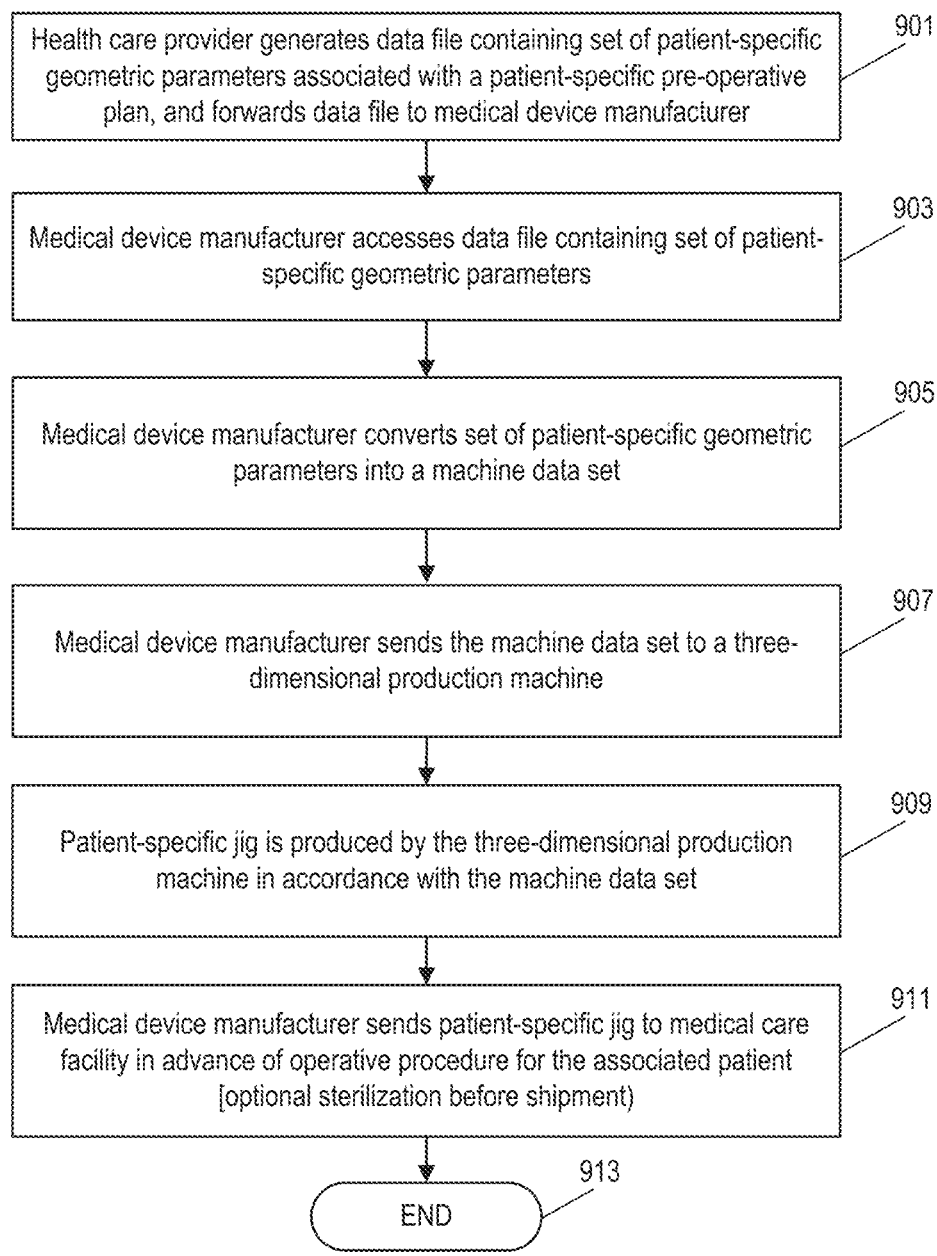
FIG. 9 is a flowchart depicting the manufacture at a medical device manufacturer of a patient-specific jig for confirmation of a longitudinal fixation element contour according to an aspect of the invention.

FIG. 9 is a flowchart depicting the manufacture at a medical device manufacturer of a patient-specific jig for confirmation of a fixation rod contour according to an aspect of the invention. In step 901, a health care provider generates a data file containing a set of patient-specific geometric parameters associated with a patient-specific pre-operative plan, and forwards, or makes available, the data file to the medical device manufacturer. Next, in step 903, the medical device manufacturer accesses the data file containing set of patient-specific geometric parameters. The medical device manufacturer converts the set of patient-specific geometric parameters into a machine data set in step 905. Medical device manufacturer sends the machine data set to a three-dimensional production machine in step 907, and then the patient-specific jig is produced by the three-dimensional production machine in accordance with the machine data set in step 909. Next, in step 911, the medical device manufacturer sends the patient-specific jig to a medical care facility in advance of operative procedure for the associated patient. The medical device manufacturer may optionally sterilize the patient-specific jig before sending it to the medical care facility. The method then ends at step 913. These steps may be performed in accordance with the description provided above with respect to FIG. 8.

Figure 10:
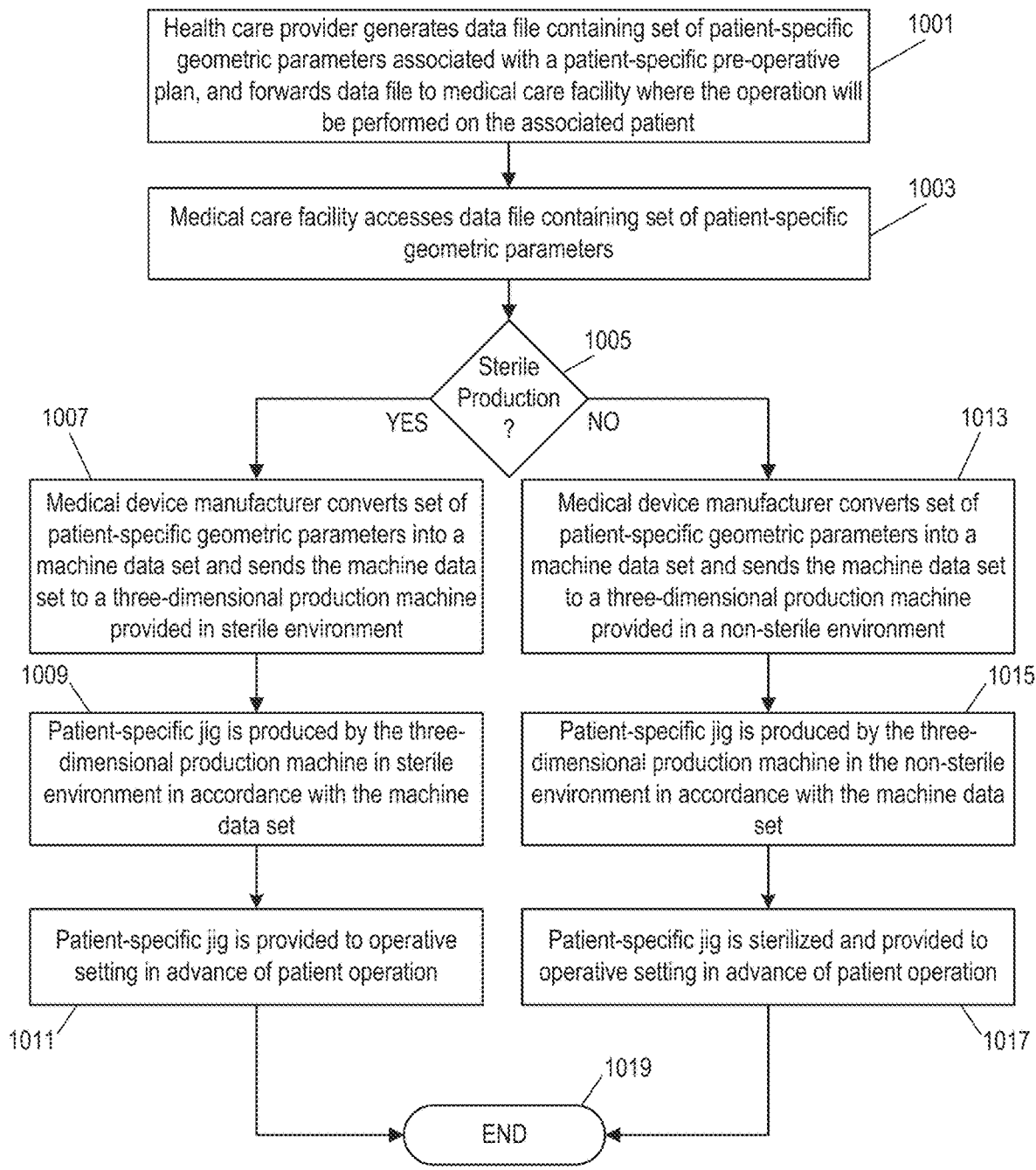
FIG. 10 is a flowchart depicting the manufacture at a medical care facility of a patient-specific jig for confirmation of a longitudinal fixation element contour according to an aspect of the invention.

FIG. 10 is a flowchart depicting the manufacture at a medical care facility of a patient-specific jig for confirmation of a fixation rod contour according to an aspect of the invention. In step 1001, a health care provider, such as a doctor or surgeon, generates a data file containing a set of patient-specific geometric parameters associated with a patient-specific pre-operative plan, and forwards the data file to a medical care facility where the operation will be performed on the associated patient. Next, in step 1003, the medical care facility accesses the data file containing the set of patient-specific geometric parameters and a determination is made in step 1005 whether or not to produce the patient-specific jig in a sterile environment. If so, the process proceeds to step 1007 in which the medical device manufacturer converts the set of patient-specific geometric parameters into a machine data set and sends the machine data set to a three-dimensional production machine provided in sterile environment. Then, in step 1009, the patient-specific jig is produced by the three-dimensional production machine in sterile environment in accordance with the machine data set. The patient-specific jig is then provided to an operative setting in advance of the patient operation in step 1011. The process then ends at step 1019.

If it is determined in step 1005 not to produce the patient-specific jig in a sterile environment, then the process proceeds to step 1013 in which the medical device manufacturer converts the set of patient-specific geometric parameters into a machine data set and sends the machine data set to a three-dimensional production machine provided in non-sterile environment. Then, in step 1015, the patient-specific jig is produced by the three-dimensional production machine in the non-sterile environment in accordance with the machine data set. The patient-specific jig is then sterilized and provided to an operative setting in advance of the patient operation in step 1017. The process then ends at step 1019.

Figure 11:
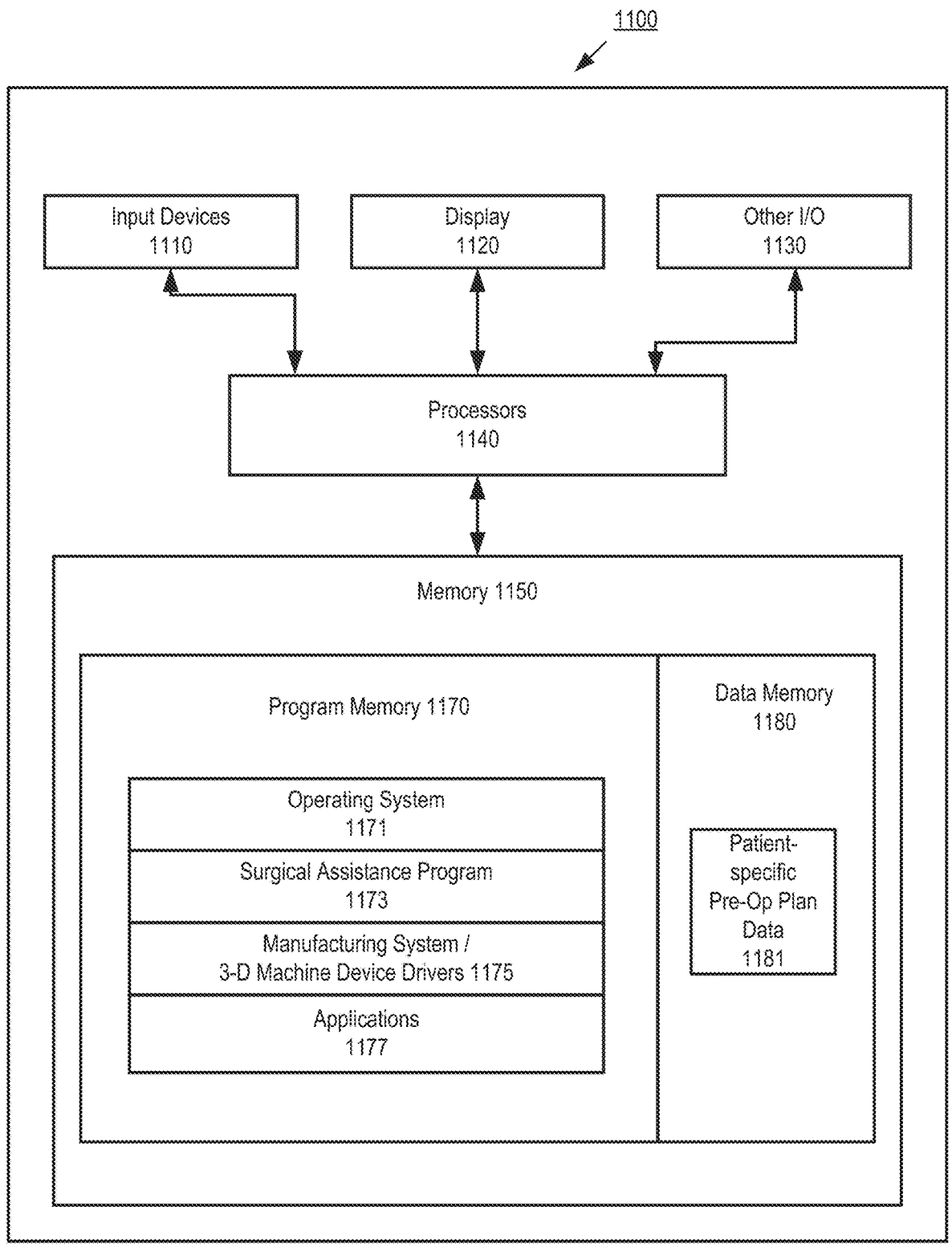
FIG. 11 is a functional diagram depicting a computing system for use in the manufacture of a patient-specific jig for confirmation of a longitudinal fixation element contour according to an aspect of the invention.

FIG. 11 is a functional diagram depicting a computing system for use in the manufacture of a patient-specific jig for confirmation of a fixation rod contour according to an aspect of the invention. In FIG. 11, computing system 1100 is shown to include one or more input devices 1110 that provide input to processor(s) 1140 (e.g., CPU(s), GPU(s), HPU(s), etc.). Input devices 1110 allow a user to input signals or actions representing instructions and/or data for use by computing system 1100 and can be used to manipulate a model of the spine. The signals or actions provided by input devices 1110 can be mediated by a hardware controller that interprets the signals received from the input device and communicates the information or data to processors 1140 using a communication protocol. Input devices 1110 include, for example, a mouse, a keyboard, a touchscreen, an infrared sensor, a touchpad, a wearable input device, a camera- or image-based input device, a microphone, or other input devices. Processors 1140 can be a single processing unit or multiple processing units in a device or distributed across multiple devices. Processors 1140 can be coupled to other hardware devices, for example, with the use of a bus, such as a PCI bus or SCSI bus or other known computer bus.

Computing system 1100 includes display 1120 that may be used to display text, images, models, web pages, virtual procedures, surgical plans, implants, and graphics. Display 1120 may be a touch-screen display in which displayed image(s), models, text, web pages, etc. can be displayed and manipulated using typical touch-screen gestures. Display 1120 may be an LCD display screen, an LED display screen, a projected, holographic, or augmented reality display (such as a heads-up display device or a head-mounted device), and so on. Other I/O devices 1130 are also coupled to processors 1140 and may be I/O devices such as a network card, video card, audio card, USB, firewire or other external device, camera, printer, speakers, CD-ROM drive, DVD drive, disk drive, or Blu-Ray device. Other I/O 1130 can also include input ports for obtaining information directly from connected medical equipment such as imaging apparatuses, including MRI machines, X-Ray machines, CT machines, etc. Other I/O 1130 can further include input ports for receiving data from these types of machine from other sources, such as across a network or from previously captured data, for example, stored in a remote server or database.

Other I/O 1130 may also include a communication device capable of communicating wirelessly or via a wire connection with a network node. The communication device can communicate with another device or a server through a network using, for example, TCP/IP protocols. Computing system 1100 can utilize the communication device to distribute operations across multiple network devices, including imaging equipment, manufacturing equipment, etc.

Computing system 1100 includes memory 1150 which is coupled to processors 1140. Memory 1150 can be provided in a single memory device or distributed across multiple memory devices. Memory 1100 includes one or more of various hardware devices for volatile and non-volatile storage and can include both read-only and writable memory. For example, memory 1150 can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. Memory 1150 is not a propagating signal divorced from underlying hardware and is therefore non-transitory. Memory 1150 includes program memory 1170 that stores programs and software, such as for example an operating system 1171, surgical assistance system 1173, manufacturing system and 3-D machine device drivers 1175 and other application programs 1177, such as program for managing a data hub. Memory 1150 also includes data memory 1180 that can include patient-specific preoperative plan data 1181 such as, e.g., patients data (name, DOB, gender, contact information, consent, scan data, etc.), implant information, configuration data, settings, user options or preferences, etc., which can be provided to the program memory 1170 or any element of the computing system 1100. Specifically, patient-specific preoperative plan data 1181 may include patient-specific geometric parameters that represent a contoured curve of one or more fixation rods for use in a patient operation.

The present technology includes a method for designing patient-specific jigs, orthopedic implants, and/or fixation elements of patients. The method can include receiving a patient data set of the subject patient. The patient data set can include spinal pathology data for the subject patient. The patient data set can be analyzed to provide a patient-specific technology, such as an implant jig or template that can be used during surgery to confirm that a contoured longitudinal fixation element, such as a fixation rod, conforms to predetermined parameters of a patient-specific pre-operative plan. In some embodiments, the patient data set can be compared to a plurality of reference patient data sets to identify one or more similar patient data sets in the plurality of reference patient data sets, with each identified similar patient data set corresponding to a reference patient having similar spinal pathology to the subject patient and who received treatment with technology. For example, each of the reference patients can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries. The present technology can incorporate and include technology of U.S. application Ser. No. 17/124,822, which is incorporated by reference.

The method can further include selecting a subset of the one or more similar patient data sets based on whether the similar patient data sets indicated the reference patient had a favorable outcome (e.g., a favorable orthopedic implant subsidence outcome, one or more improved or corrected anatomical metrics, presence of fusion, improved HRQL, etc.) following implantation of their orthopedic implant. The method can further include identifying, for at least one similar reference patients of the selected subset, surgical procedure data and design data for the respective orthopedic implant that produced the favorable outcome in the similar reference patient. Based on the design data and the surgical produced data that produced the favorable outcome in the similar reference patient, the patient-specific orthopedic implant for the subject patient and a surgical procedure for implanting the patient-specific orthopedic implant into the subject patient can be designed. In some embodiments, the method can further include outputting fabrication instructions for causing a manufacturing system to manufacture the patient-specific orthopedic implant according to the generated design. In representative embodiments, the foregoing method can be performed by a system storing computer-executable instructions that, when executed, cause the system to perform the steps of method.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/352,699, filed on Mar. 13, 2019, titled "SYSTEMS AND METHODS FOR ORTHOPEDIC IMPLANT FIXATION;"

U.S. application Ser. No. 16/383,215, filed on Apr. 12, 2019, titled "SYSTEMS AND METHODS FOR ORTHOPEDIC IMPLANT FIXATION;"

U.S. application Ser. No. 16/569,494, filed on Sep. 12, 2019, titled "SYSTEMS AND METHODS FOR ORTHOPEDIC IMPLANTS;" and U.S. Application No. 62/773,127, filed on Nov. 29, 2018, titled "SYSTEMS AND METHODS FOR ORTHOPEDIC IMPLANTS."

U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS;"

U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS;"

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS;"

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS;"

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS;"

U.S. Patent Application No. 63/116,436, filed Nov. 20, 2021, "PATIENT-SPECIFIC JIG FOR PERSONALIZED SURGERY;"

U.S. application Ser. No. 17/100,396, filed Nov. 20, 2020, titled "PATIENT-SPECIFIC VERTEBRAL IMPLANTS WITH POSITIONING FEATURES;" and International Patent Application No. PCT/US21/12065, filed Jan. 4, 2021, titled "PATIENT-SPECIFIC MEDICAL PROCEDURES AND DEVICES, AND ASSOCIATED SYSTEMS AND METHODS."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

It should be appreciated that the materials used for the devices and products of manufacture described above are illustrative and that other materials can be used for such devices and products of manufacture without departing from the invention. Similarly, sizes, shapes and contours of the devices and products of manufacture described above are illustrative and a person of skill in the art will understand that other sizes, shapes and contours can also be used for such devices and products of manufacture without departing from the invention.

Those of skill in the art will appreciate that the various method steps, illustrative logical and functional blocks, modules, units, and algorithm steps described in connection with the aspects disclosed herein can often be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular constraints imposed on the overall system and devices. Skilled persons can implement the described functionality in varying ways for each particular system, but such implementation decisions should not be interpreted as causing a departure from the scope of the invention described herein. In addition, the grouping of functions within a unit, module, block, or step is for ease of description. Specific functions or steps can be moved from one unit, module, or block without departing from the invention.

Some or all of the various illustrative methods, algorithms, logical and functional blocks, units, steps and modules described in connection with the aspects disclosed herein, and those provided in the accompanying documents, can be implemented or performed with a processor, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein, and those provided in the accompanying documents. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm and the processes of a block or module described in connection with the aspects disclosed herein, and those provided in the accompanying documents, can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC. Additionally, devices, blocks, or modules that are described as coupled may be coupled via intermediary devices, blocks, or modules. Similarly, a first device may be described as transmitting data to (or receiving from) a second device wherein there are intermediary devices that couple the first and second device and also wherein the first device and/or second device is unaware of the ultimate destination of the data.

The above description of the disclosed aspects, and that provided in the accompanying documents, is provided to enable any person skilled in the art to make or use the invention. Various modifications to these aspects will be readily apparent to those skilled in the art, and the generic principles described herein, and in the accompanying documents, can be applied to other aspects without departing from the spirit or scope of the invention. Thus, it is to be understood that the description and drawings presented herein, and presented in the accompanying documents, represent particular aspects of the invention and are therefore representative examples of the subject matter that is broadly contemplated by the present invention. It is further understood that the scope of the present invention fully encompasses other aspects that are, or may become, understood to those skilled in the art based on the descriptions presented herein and that the scope of the present invention is accordingly not limited by the descriptions presented herein, or by the descriptions presented in the accompanying documents.

What is claimed is:

1. A method for manufacturing a patient-specific jig for use in confirming a correct contour of a fixation element in an operative setting, the method comprising the steps of:
    accessing a data file containing patient-specific geometric parameters associated with a modeled patient-specific anatomical correction of a native anatomy of a particular patient based on a patient-specific pre-operative plan for the particular patient;
    obtaining one or more fixation element design criteria based at least in part on one or more reference patient data sets, wherein the reference patient data sets include data from patients other than the particular patient;
    designing the patient-specific jig to include a patient-specific contoured curve based on the patient-specific geometric parameters and the one or more fixation element design criteria;
    converting the patient-specific jig design into a machine data set for use by a three-dimensional production machine; and
    sending the machine data set to the three-dimensional production machine upon which the patient-specific jig is produced by the three-dimensional production machine in accordance with the machine data set.

2. The method of claim 1 wherein the data file is accessed from a remote server via an internet connection.

3. The method of claim 1 wherein the data file is accessed from a from a patient-specific implant design system.

4. The method of claim 1 wherein the patient-specific geometric parameters define a contoured curve of a fixation element for attachment to a plurality of spine segments.

5. The method of claim 1 wherein a manufacturing software system is used to convert the patient-specific geometric parameters into a machine data set.

6. The method of claim 1 wherein a machine-specific software driver unit is used to convert the patient-specific geometric parameters into a machine data set.

7. The method of claim 1 wherein the three-dimensional production machine is an additive manufacturing machine.

8. The method of claim 1 wherein the three-dimensional production machine is a three-dimensional printer.

9. The method of claim 1 wherein the three-dimensional production machine is a subtractive manufacturing machine.

10. The method of claim 9 wherein the subtractive manufacturing machine is a three-dimensional computer numerical control (CNC) machine.

11. The method of claim 1 wherein the patient-specific jig is produced by the three-dimensional production machine using at least one of titanium, stainless steel, a metal alloy, and a plastic material.

12. A patient-specific jig manufactured by a process comprising:
- accessing a data file containing patient-specific geometric parameters associated with a modeled patient-specific anatomical correction of a native anatomy of a particular patient based on a patient-specific pre-operative plan for the particular patient;
- obtaining one or more fixation element design criteria based at least in part on one or more reference patient data sets, wherein the reference patient data sets include data from patients other than the particular patient;
- designing the patient-specific jig to include a patient-specific contoured curve based on the patient-specific geometric parameters and the one or more fixation element design criteria;
- converting the patient-specific jig design into a machine data set for use by a three-dimensional production machine; and
- sending the machine data set to the three-dimensional production machine upon which the patient-specific jig is produced by the three-dimensional production machine in accordance with the machine data set.

13. The patient-specific jig of claim 12 wherein the data file is accessed from a remote server via an internet connection.

14. The patient-specific jig of claim 12 wherein the data file is accessed from a patient-specific implant design system.

15. The patient-specific jig of claim 12 wherein the patient-specific geometric parameters define a contoured curve of a fixation element for attachment to a plurality of spine segments.

16. The patient-specific jig of claim 12 wherein a manufacturing software system is used to convert the patient-specific geometric parameters into a machine data set.

17. The patient-specific jig of claim 12 wherein a machine-specific software driver unit is used to convert the patient-specific geometric parameters into a machine data set.

18. The patient-specific jig of claim 12 wherein the three-dimensional production machine is an additive manufacturing machine.

19. The patient-specific jig of claim 12 wherein the three-dimensional production machine is a three-dimensional printer.

20. The patient-specific jig of claim 12 wherein the three-dimensional production machine is a subtractive manufacturing machine.

21. The patient-specific jig of claim 20 wherein the subtractive manufacturing machine is a three-dimensional computer numerical control (CNC) machine.

22. The patient-specific jig of claim 12 wherein the patient-specific jig is produced by the three-dimensional production machine using at least one of titanium, stainless steel, a metal alloy, and a plastic material.

23. A method for manufacturing a patient-specific jig by a medical device manufacturer, the method comprising the steps of:
- accessing a data file containing patient-specific geometric parameters associated with a modeled patient-specific anatomical correction of a native anatomy of a particular patient based on a patient-specific pre-operative plan for the particular patient;
- obtaining one or more fixation element design criteria based at least in part on one or more reference patient data sets, wherein the reference patient data sets include data from patients other than the particular patient;
- designing the patient-specific jig to include a patient-specific contoured curve based on the patient-specific geometric parameters and the one or more fixation element design criteria;
- converting the patient-specific jig design into a machine data set for use by a three-dimensional production machine provided at a facility of the medical device manufacturer;
- sending the machine data set to the three-dimensional production machine;
- producing the patient-specific jig with the three-dimensional production machine in accordance with the machine data set; and
- sending the patient-specific jig from the medical device manufacturer to a medical care facility where an operative procedure is scheduled to be performed on the particular patient associated with the patient-specific pre-operative plan.

24. The method of claim 23 wherein the three-dimensional production machine is provided in a sterile location of the medical device manufacturer.

25. The method of claim 23 wherein the three-dimensional production machine is provided in a non-sterile location of the medical device manufacturer and wherein the method further includes the step of sterilizing the patient-specific jig before sending the patient-specific jig to the medical care facility.

26. The method of claim 23 wherein the data file is accessed by the medical device manufacturer from a remote server via an internet connection.

27. The method of claim 26 wherein the remote server is in a health care provider system.

28. The method of claim 23 wherein the data file is accessed by the medical device manufacturer from a from a patient-specific implant design system.

29. The method of claim 23 wherein the patient-specific geometric parameters define a contoured curve of a fixation element for attachment to a plurality of spine segments.

30. The method of claim 23 wherein a manufacturing software system is used to convert the patient-specific geometric parameters into a machine data set.

31. The method of claim 23 wherein a machine-specific software driver unit is used to convert the patient-specific geometric parameters into a machine data set.

32. The method of claim 23 wherein the three-dimensional production machine is an additive manufacturing machine.

33. The method of claim 23 wherein the three-dimensional production machine is a three-dimensional printer.

34. The method of claim 23 wherein the three-dimensional production machine is a subtractive manufacturing machine.

35. The method of claim 34 wherein the subtractive manufacturing machine is a three-dimensional computer numerical control (CNC) machine.

36. The method of claim 23 wherein the patient-specific jig is produced by the three-dimensional production machine using at least one of titanium, stainless steel, a metal alloy, and a plastic material.

37. A method for manufacturing a patient-specific jig at a medical care facility, the method comprising the steps of:
- accessing, at the medical care facility, a data file containing patient-specific geometric parameters associated with a modeled patient-specific anatomical correction of a native anatomy of a particular patient based on a patient-specific pre-operative plan for the particular patient;

obtaining, at the medical care facility, one or more fixation element design criteria based at least in part on one or more reference patient data sets, wherein the reference patient data sets include data from patients other than the particular patient;

designing the patient-specific jig to include a patient-specific contoured curve based on the patient-specific geometric parameters and the one or more fixation element design criteria;

converting the patient-specific jig design into a machine data set for use by a three-dimensional production machine provided at the medical care facility;

sending the machine data set to the three-dimensional production machine; and producing the patient-specific jig with the three-dimensional production machine in accordance with the machine data set.

38. The method of claim 37 wherein the three-dimensional production machine is provided in a sterile location of the medical care facility.

39. The method of claim 37 wherein the three-dimensional production machine is provided in a non-sterile location of the medical care facility and wherein the method further includes the step of sterilizing the patient-specific jig.

40. The method of claim 37 wherein the data file is accessed by the medical care facility from a remote server via an internet connection.

41. The method of claim 40 wherein the remote server is in a health care provider system.

42. The method of claim 37 wherein the data file is accessed by the medical care facility from a from a patient-specific implant design system.

43. The method of claim 37 wherein the patient-specific geometric parameters define a contoured curve of a fixation element for attachment to a plurality of spine segments.

44. The method of claim 37 wherein a manufacturing software system is used to convert the patient-specific geometric parameters into a machine data set.

45. The method of claim 37 wherein a machine-specific software driver unit is used to convert the patient-specific geometric parameters into a machine data set.

46. The method of claim 37 wherein the three-dimensional production machine is an additive manufacturing machine.

47. The method of claim 37 wherein the three-dimensional production machine is a three-dimensional printer.

48. The method of claim 37 wherein the three-dimensional production machine is a subtractive manufacturing machine.

49. The method of claim 48 wherein the subtractive manufacturing machine is a three-dimensional computer numerical control (CNC) machine.

50. The method of claim 37 wherein the patient-specific jig is produced by the three-dimensional production machine using at least one of titanium, stainless steel, a metal alloy, and a plastic material.

51. The method of claim 37 wherein the patient-specific jig is produced by the three-dimensional production machine in a sterile location of the medical care facility.

52. The method of claim 37 wherein the patient-specific jig is produced by the three-dimensional production machine in a sterile location of the medical care facility.

53. A method for manufacturing a patient-specific jig, the method comprising the steps of:

accessing a data file containing imaging data that represents bony anatomy associated with a particular patient;

generating a model of the bony anatomy of the particular patient in a virtual space;

correcting anatomical relationships of the bony anatomy in the virtual space;

measuring, from the corrected model, one or more patient-specific geometric parameters associated with the corrected anatomical relationships;

modelling a path of a fixation element between a plurality of bony anatomical landmarks associated with the corrected anatomical relationships of the bony anatomy in the virtual space, wherein the modeled path of the fixation element is based in part on the measured patient-specific geometric parameters associated with the corrected anatomical relationships;

obtaining one or more fixation element design criteria based at least in part on one or more reference patient data sets, wherein the reference patient data sets include data from patients other than the particular patient designing the patient-specific jig with a patient-specific contoured curve based on the modeled path of the fixation element and the one or more fixation element design criteria; and producing the patient-specific jig with a three-dimensional production machine, wherein the patient-specific jig conforms to the modeled path of the fixation element.

54. The method of claim 53, further comprising:

generating a virtual model of the bony anatomy based on the imaging data for the correction of the anatomical relationships;

virtually simulating positioning of the fixation element using the virtual model with the corrected anatomical relationships;

generating a design of the fixation element based on the virtual simulation; and designing the patient-specific jig based on the design of the fixation element.

55. The method of claim 53, wherein the patient-specific jig is substantially geometrically congruent to the modeled path of the fixation element.

56. The method of claim 53, further comprising:

simulating manufacturing of the patient-specific jig using one or more virtual three-dimensional models;

identifying one or more fixation element design criteria based on the patient's anatomy and the simulation of the manufacturing of the patient-specific jig; and generating a manufacturing plan according to the identified one or more fixation element design criteria.

57. The method of claim 56, wherein the one or more fixation element design criteria include one or more of surface finish, mechanical strength, biocompatibility, and/or target service life.

58. The method of claim 56, further comprising:

comparing a design for the patient-specific jig to reference jig designs;

selecting a set of the references jigs designs identified as similar to the design for the patient-specific jig; and generating a manufacturing plan for producing the patient-specific jig using the three-dimensional production machine based on manufacturing parameters associated with the set of the references jigs designs.

59. The method of claim 56, further comprising:

accessing a patient-specific surgical plan for the patient, the patient plan includes usage of the fixation element; and designing the patient-specific jig further based at least partially on the patient-specific surgical plan.

* * * * *